United States Patent
Morimoto et al.

[11] Patent Number: 5,806,521
[45] Date of Patent: Sep. 15, 1998

[54] COMPOSITE ULTRASOUND IMAGING APPARATUS AND METHOD

[75] Inventors: Alan K. Morimoto; Wallace J. Bow, Jr.; David Scott Strong; Fred M. Dickey, all of Albuquerque, N. Mex.

[73] Assignee: Sandia Corporation, Albuquerque, N. Mex.

[21] Appl. No.: 622,129

[22] Filed: Mar. 26, 1996

[51] Int. Cl.⁶ ....................................................... A61B 8/00
[52] U.S. Cl. ........................................ 128/661.01; 73/625
[58] Field of Search ....................... 128/660.07, 660.08, 128/660.09, 661.01, 916, 661.08, 661.09, 661.1, 660.04, 660.05; 73/625, 626

[56] References Cited

U.S. PATENT DOCUMENTS

| 5,379,769 | 1/1995 | Ito et al. .................................. 128/916 |
| 5,485,842 | 1/1996 | Quistgaard ........................ 128/660.07 |
| 5,529,070 | 6/1996 | Augustine et al. ................ 128/660.07 |

*Primary Examiner*—George Manuel
*Attorney, Agent, or Firm*—Dennis Armijo; Gregory A. Cone

[57] ABSTRACT

An imaging apparatus and method for use in presenting composite two dimensional and three dimensional images from individual ultrasonic frames. A cross-sectional reconstruction is applied by using digital ultrasound frames, transducer orientation and a known center. Motion compensation, rank value filtering, noise suppression and tissue classification are utilized to optimize the composite image.

40 Claims, 37 Drawing Sheets

COMPOSITE ULTRASOUND IMAGING APPARATUS AND METHOD

This invention was made with Government support under Contract DE-AC04-94AL85000 awarded by the U.S. Department of Energy. The Government has certain rights in the invention.

BACKGROUND OF THE INVENTION

1. Field of the Invention (Technical Field)

The invention relates to imaging and more particularly to an apparatus and method of creating composite two dimensional (2D) or three dimensional (3D) video presentations utilizing ultrasound image data.

2. Background Art

Creating 2D or 3D images from different image sources is taught in several patents such as U.S. Pat. No. 5,099,846, to Hardy. However, the image data utilized in these devices is limited to expensive image sources such as computed tomography (CT), nuclear magnetic resonance (NMR), X-ray, and other known imaging modalities. These image sources contain sharp or clear image data, therefore filtering or image manipulation is relatively easy to do. The use of ultrasound images in these systems is absent due to the complexity of defining internal targets as opposed to mere surface location.

Complete images, including skin and bone have been obtained using either X-ray computer-assisted tomography (CT) or magnetic resonance imaging (MRI) but these methods have multiple disadvantages. Both of these procedures are costly and slow. Typical CT and MRI machines will cost several million dollars for initial purchase and can cost hundreds of thousands of dollars more for specialized facilities that provide shielding of patients and personnel. Furthermore, x-ray CT uses ionizing radiation that has been determined harmful to humans. Most computer workstations for this technology are based on proprietary technology and are limited to their ability to interface with other data processing systems. Because of these problems neither CT nor MRI systems are practical for regular use.

The present invention can be beneficial as a medical diagnostic tool, for example, for locating broken bones, certain targets or foreign objects in a body. Due to the small size and comparably inexpensive cost of an ultrasound system, the invention can be invaluable in the field or in a clinical setting where other more expensive imaging sources are not available.

Another example for the use of 3D ultrasound images is in the manufacture of prosthesis'. To accommodate individual differences current practice is to custom make each prosthesis. This process is time consuming, costly and requires a highly skilled prosthetist. Although prostheses have been improved in quality over the years based on improvements in the manual techniques and in the use of new materials, the basic techniques remain largely the same as in previous generations.

As patients walk and age, their residual limbs change shape due to atrophy of the soft tissue, as well as callousing, edema, scar tissue development, aging, and other complex processes. These changes alter the limb/socket interface and can result in pain or skin breakdown. The average amputee will need three to five new prostheses within the first five years after amputation because of changes in the residual limb that result in "socket failure". For each new prosthesis, the patient must undergo the entire measuring the fitting process and the prosthetist must begin anew the design and fabrication processes.

This situation is complicated by the fact that current design and fabrication procedures are more an artisan's craft than a science. Construction of the patellar-tendon-bearing (PTB) type device, which is best suited to ambulation of below-the-knee (BK) amputees, involves techniques that are labor intensive and result in inconsistent products. Acquiring data about the shape of the limb and identifying weight-bearing and potentially sensitive areas are critical early steps in ensuring an effective fit. It is important to note that the weight-bearing and sensitive areas are in close proximity to the underlying bone structure. It is necessary to modify the socket shape to provide pressure relief directly over bony prominences because pressure in these areas will cause immediate skin breakdown. Additionally, it is necessary to modify the socket shape to support the patient in areas that can bear weight. These weight bearing areas are identified by their proximity to the underlying bone structure. The prosthetist uses his/her experience and knowledge of anatomy to approximate locating the bone structure.

There are several disadvantages of this method. First, because the process is manual, the final fit depends entirely on the precision modeling of the leg. That leg model is generated in a step-by-step method that can create errors at each step. Second, the original model of the leg is not preserved during this process. Therefore, if at the end of fabrication, the prosthesis does not fit and cannot be adjusted, the entire process must be repeated. Finally, because the process is labor intensive and takes several days, the product is expensive.

As an alternative method to manual socket fabrication, computer-aided design and manufacturing techniques are now being applied to the problem of designing prosthetic sockets. The data required at the initial stage of socket design involves converting measures of residual limb shape into a computer-readable format. Several researchers have discussed methods of gathering shape data including the use of silhouettes, as shown in "Silhouette Shape Sensor", Smith, et al., *Bioengineering Centre Report.*, pp. 41–42 (1986), digitizers, "Shoe Last Replication by Moire Contourography", Vickers, et al., *Proceedings of the 4th Rehabilitation Engineering Conference*, Washington D.C., August 1981, Shadow Moire Contourography, "Moire Contourography and Computer Aided Replication of Human Anatomy", Duncan, et al., *I Mech. Eng.* 9, 1980; "Shape Sensing for Computer-Aided Below-Knee Prosthetic Design", Fernie, et al., *Prosth. Orth. Int.*, 9:12–16, 1985, light streak shape sensing, *Proceedings of the '89 RESNA Annual Conference*, New Orleans, La. June 1989; "Computerized Tomography as an Aid to Prosthetic Socket Design", Faulkner, et al., *Rehab. R&D Prog. Rpt.*, 1:7–8, 1987, computer assisted tomography, "An Ultrasound Shape Sensing Mechanism", Faulkner, et al., *Presented at the 13th Annual Meeting of the American Academy of Orthotics and Prosthetists*, Tampa Fla. 1987, magnetic resonance imaging, "CAD/CAM System Applied to the Foot Shape for Prosthetic Device", Oshima, et al., *Proceedings of the RESNA 8th Annual Conference*, pp. 222–224, 1985, and linear potentiometers, "Socket Form Analysis of Computed Tomography Data", Faulkner, et al, *Journal of Prosthetics and Orthotics*, 1(3):154–164, 1989. Most of the work in this area has focused on utilizing surface shape data.

The most commonly used alternative system of acquiring shape data employs a mechanical digitizer that measures the inside of a plaster mold of the patient's residual limb. It provides relatively low resolution because of its indirect nature and is not effective in digitizing the distal end of the residual limb. Non-contact laser imagers can also provide shape information. Scanning is completed in just a few seconds and relatively high resolution data can be acquired. Mechanical digitizers and laser imagers only generate surface topology data.

SUMMARY OF THE INVENTION
(DISCLOSURE OF THE INVENTION)

In accordance with the present invention there is provided an apparatus and method for providing two dimensional or three dimensional images from an ultrasound transducer. The preferred apparatus of the invention is an apparatus generating a video presentation of ultrasound images comprising at least one ultrasound transducer, apparatus for acquiring a plurality of ultrasound images in scan increments of an object, an apparatus for converting the acquired images into a selected format, an apparatus for storing the converted images and apparatus for registering the converted images to generate a composite image of the object.

The preferred at least one ultrasound transducer comprises a two dimensional array of ultrasound transducers.

The preferred apparatus for acquiring a plurality of ultrasound images comprises a apparatus for acquiring data from known orientations and positions. The orientations comprise angles from a home orientation. The preferred apparatus for acquiring data from known orientations and positions comprises a feedback apparatus for optimizing a next scan. The preferred feedback apparatus comprises an apparatus for reorienting the at least one ultrasound transducer based on a previous scan's signal quality.

The preferred apparatus for acquiring data from known orientations and positions comprises a filter apparatus for acquired data reduction. The preferred filter apparatus comprises rank value filtering.

The preferred apparatus for acquiring data from known orientations and positions comprises overlapping converted images. The overlapping converted images comprise vertical overlapping images. The overlapping converted images also can comprise horizontal overlapping images. The overlapping converted images can also comprise overlapping images in any known angle between horizontal and vertical.

The preferred apparatus for acquiring data from known orientations and positions comprises a position transducer. The preferred position transducer comprises a member selected from the group of encoders, potentiometers, LVDT's, resolvers, magnetic encoders, and inductosync apparatuses. The apparatus for generating a video presentation with a position transducer further comprises a tachometer.

The preferred scan increments comprise surface normal optimization. The preferred scan increments comprise the composite image with an optimized intensity of predetermined anatomical features of the object. The preferred apparatus for registering comprises a transformation matrix apparatus for realignment of converted image data relative to home position orientation.

The apparatus for registering can further comprises an apparatus for object motion compensation. The preferred apparatus for object motion compensation comprises correlating overlapping converted image data. The preferred apparatus for acquiring data from known orientations and positions comprises apparatus for determining coordinates for selected targets within the object from the converted images.

A preferred method of generating a video presentation of ultrasound images comprises the steps of providing at least one ultrasound transducer, acquiring a plurality of ultrasound images in scan increments of an object, converting the acquired images into a selected format, storing the converted images and registering the converted images to generate a composite image of the object. The preferred step of providing at least one ultrasound transducer comprises providing a two dimensional array of ultrasound transducers. The preferred step of acquiring a plurality of ultrasound images comprises acquiring data from known orientations and positions.

The alternative step of acquiring data from known orientations comprises acquiring angle data from a home orientation. The alternative step of acquiring data from known orientations and positions comprises optimizing a next scan with feedback from a prior scan.

The preferred feedback comprises reorienting the at least one transducer based on a previous scan's signal quality. The preferred step of acquiring data from known orientations and positions comprises providing a filter for acquired data reduction. The preferred filter comprises rank value filtering.

The preferred step of acquiring data from known orientations and positions comprises overlapping converted images. The preferred step of overlapping converted images comprise vertically overlapping images. The alternative step of overlapping converted images comprise horizontally overlapping images. Another alternative step of overlapping converted images comprise overlapping images in any known angle between horizontal and vertical.

The preferred step of acquiring data from known orientations and positions comprises providing a position transducer. The preferred step of providing a position transducer comprises providing a member selected from the group of encoders, potentiometers, LVDT's, resolvers, magnetic encoders, and inductosync apparatuses. The preferred method further comprises the step of providing a tachometer.

The preferred step of acquiring a plurality of ultrasound images in scan increments comprise optimizing surface normal. The preferred step of acquiring a plurality of ultrasound images in scan increments comprises optimizing the intensity of predetermined anatomical features of the object from the composite image. The preferred step of registering comprises realigning the converted image data relative to home position orientation with a transformation matrix.

The preferred step of registering further comprises compensating for object motion. The preferred step of compensating for object motion comprises correlating overlapping converted image data. The preferred step of acquiring data from known orientations and positions comprises determining coordinates for selected targets within the object from the converted images.

A primary object of the present invention is to create two dimensional and three dimensional video presentations from a composite of ultrasound image data.

Another object of the present invention is to provide detailed information regarding an amputees bone and muscle structure for prosthesis fabrication.

Yet another object of the present invention is to provide a diagnostic tool for imaging internal organs and structures using ultrasound image data.

A primary advantage of the present invention is its low cost compared to other imaging modalities.

Another advantage of the present invention is that it uses non-ionizing radiation.

Yet another advantage of the invention is its portability.

Still another advantage of the present invention is the speed of creating the presentation compared to other imaging modalities.

Another advantage of the present invention is its ability to clarify the composite images by motion compensation and incident rank value filtering.

Other objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS.

The accompanying drawings, which are incorporated into and form a part of the specification, illustrate several embodiments of the present invention and, together with the description, serve to explain the principles of the invention. The drawings are only for the purpose of illustrating a preferred embodiment of the invention and are not to be construed as limiting the invention. In the drawings:

FIG. 5 depicts a typical rank filtering horizontal reconstruction based on maximum signal echo;

DESCRIPTION OF THE PREFERRED
EMBODIMENTS (BEST MODES FOR
CARRYING OUT THE INVENTION)

The ultrasound apparatus and method of the present invention comprises hardware components and associated software for providing two dimensional or three dimensional images of an object. Ultrasound can be argued to be the logical choice as an imaging modality because it provides surface and subsurface information about a body part or other object to be studied. In addition, ultrasound is a non-ionizing form of radiation and currently, there are no known harmful affects from FDA approved ultrasound machines designed for medical diagnostic imaging. Ultrasound machines are relatively low in cost (less than one hundred thousand dollars) as compared to CT or MRI. Most ultrasound machines provide resolution of images within a range that is acceptable for 3D imaging. For example, if the resolution in depth is 1.0 mm and the lateral resolution is 2.0 mm, relative accuracies of each modality are comparable at 1.0 mm. Image frame rates vary depending on the number of focal zones and the dept of penetration from 30 frames per second (fps) to 7 fps. The slower frame rates reduce the speed of image acquisition. Even at 7 fps, however, a complete image set, for example of a leg, of 400 images can be acquired within 72 seconds.

There are two preferred embodiments discussed, one for prosthesis fabrication, and the other for use as a diagnostic tool. Although these are the only applications disclosed, the present invention can be utilized in other applications that presently use known scanning and imaging modalities.

Figure 1:
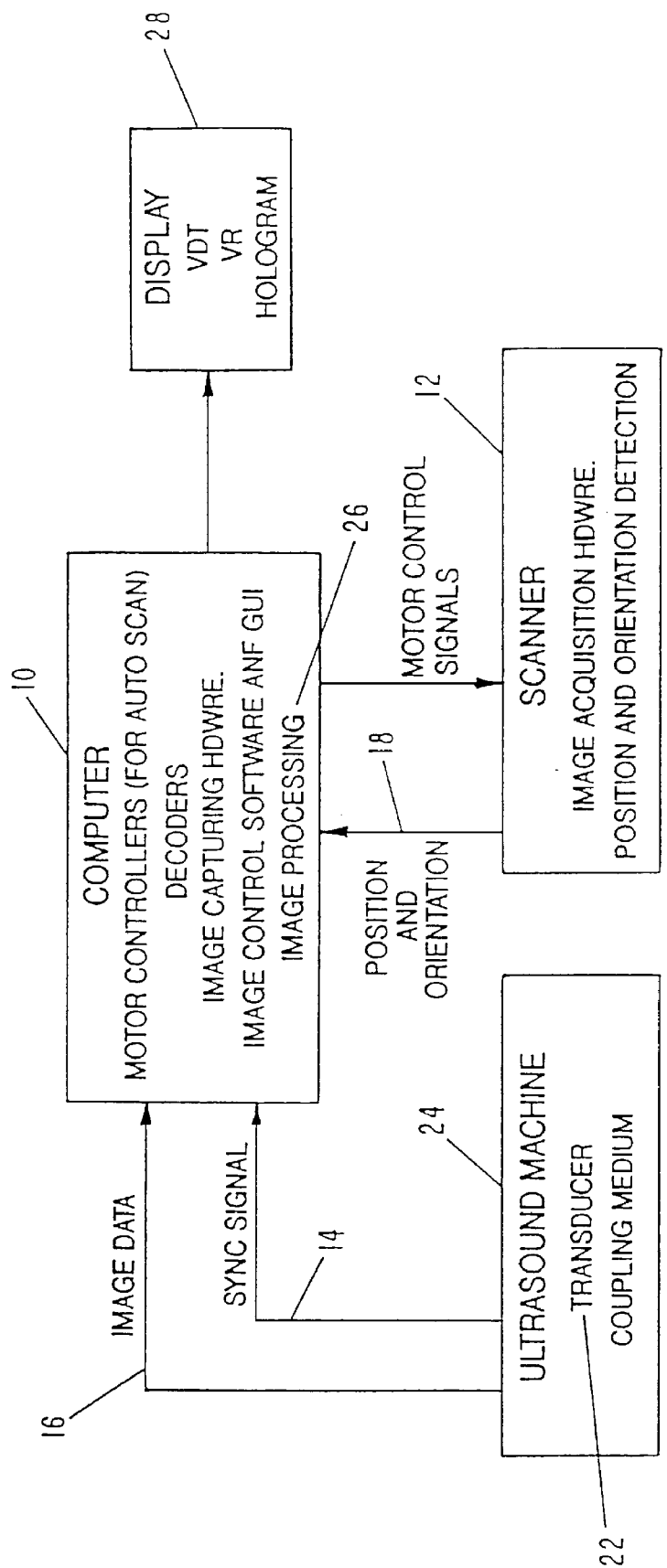
FIG. 1 is a block diagram of the preferred embodiment of the invention.

The preferred embodiment for prosthesis fabrication, of the invention is illustrated in FIG. 1. The 3D ultrasound imaging method and apparatus can be broken down into two separate sub-systems: image capturing and image processing. Image capturing comprises computer 10 that controls scanner 12 and inputs sync signal data 14, image data 16 and scanner position and orientation 18. The object to be scanned is placed in the scanning apparatus that can be automatically or manually driven, such as the one shown in FIG. 2. Referring again to FIG. 1, in the automatic mode, scanner 12 is instructed via graphical user interface (GUI) 20 within the computer 10 to scan the object with a prescribed level of precision. In the manual mode scanner 12 is instructed to accept force commands from the operator by grasping and moving the end of scanner 12. Thus scanner 12 positions and orients transducer 22 to maximize image data signal 16 to ultrasound machine 24. Ultrasound machine 24 provides images that are captured by computer 10. Both position and orientation data 18 and images are stored simultaneously in computer 10 for reconstruction purposes. GUI 20 controls the position, orientation, and resolution of each scan and can also request historical data such as patient name, date and time of scan.

The image processing subsystem takes the raw data acquired in the image capturing subsystem and forms a composite image of the anatomy that is scanned. Composite image is then processed using special image processing software 26 to enhance image quality. Motion compensation and filtering are performed prior to extraction of the skin and bone surface geometry. Image processing 26, motion compensation filtering are described herein. Data from skin and bone surface geometry can be used to fabricate custom worn devices such as prostheses.

A visual presentation of the composite images is provided via display 28.

Figure 2:
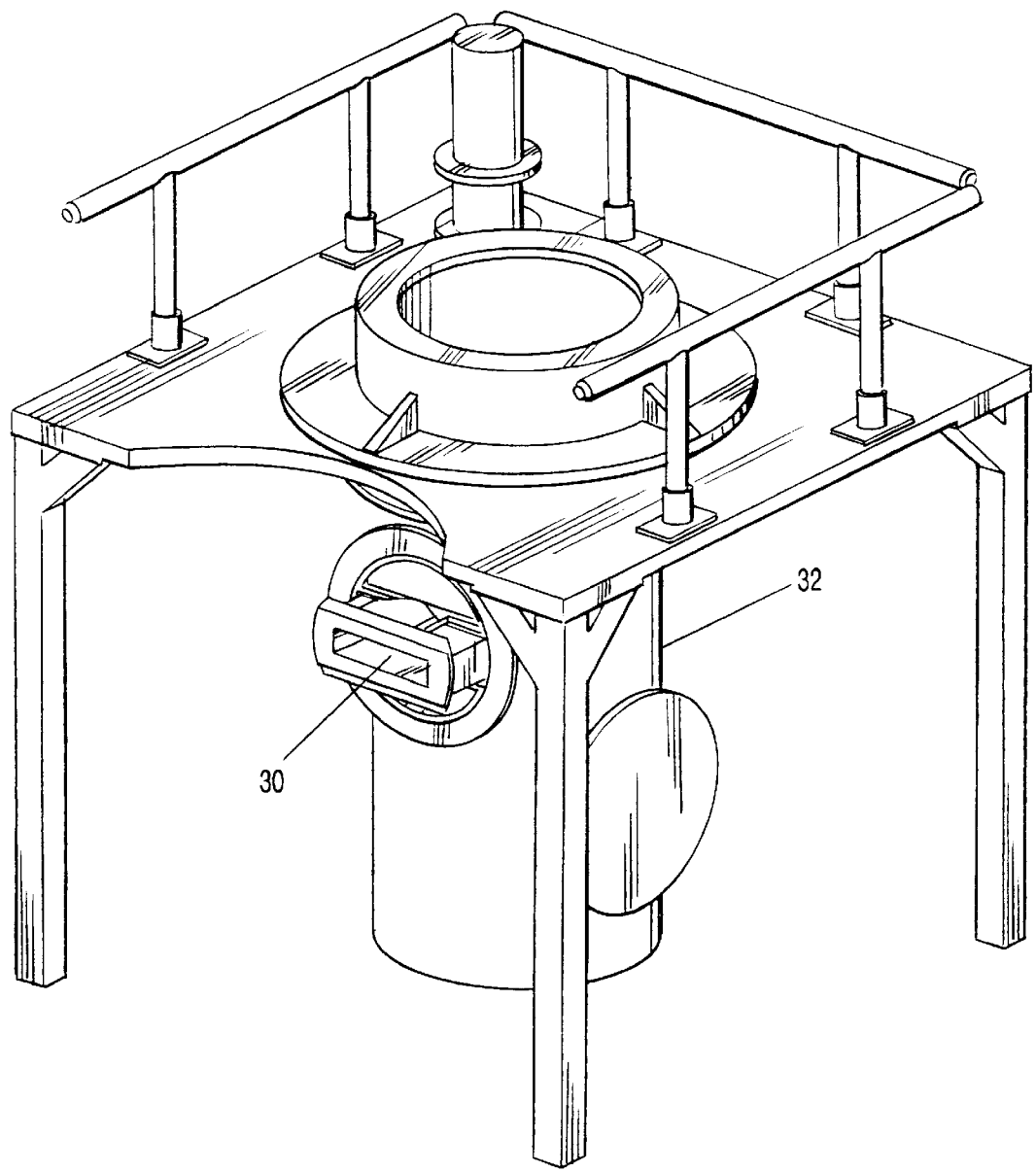
FIG. 2 illustrates the preferred hardware in accordance with the present invention.

FIG. 2 shows the preferred mechanical scanning system for prosthesis fabrication consisting of transducer holder 30, scanning tank 32, servo motor, and motor controller (not shown). Transducer holder 30 is a bracket that holds the transducer in a rigid fashion and maintains the position and orientation of the transducer in the scanning tank window. The scanning tank window is a flexible membrane that keeps water in tank 32 and allows ultrasound to penetrate without attenuation. Scanning tank 32 is filled with water for transmission of ultrasound for non-contact scanning of variable size legs. Non-contact scanning is essential for definition of "unloaded" soft tissue surfaces.

The tank diameter (preferably 11.5 inches) can be used to accommodate the largest amputee leg size while optimizing the ultrasound, penetration range. Other sized tanks can be used for different body parts or targets for scanning. For the frequency of ultrasound, preferably 3.5 MHZ, the depth of penetration is limited to 22 centimeters or 8.7 inches. At this frequency, data can be scanned beyond the center of the tank. This frequency must be altered to accommodate larger diameter tanks. Thus, any object within the tank can be imaged without strict restrictions on its location. Servo motor (not shown) is controlled by position and velocity so that the proper number of frames can be captured around the leg. With position and velocity control, the servo-controlled scanner can be varied during image capturing. Thus, leg regions that are of more interest can be scanned with finer resolution of spacing then other regions. The position of the frame capture is recorded along with the image. This information allows the image processing package to reconstruct the images based on the raw data.

The configuration of the three dimensional ultrasound scanning system allows for variations in the orientation of the ultrasound transducer. The two orientations are vertical (linear array oriented parallel to the long axis of the leg) and horizontal (linear array oriented transverse to the long axis of the leg).

With the vertical orientation, scanning of the transducer circularly around the leg generates a volumetric data set. The resolution of image spacing is measured in degrees. With variable scan rates, the bony regions of the leg are scanned with finer resolution that the soft tissue regions. Regardless of the resolution of image capture, there remains a space between captured data sets that is unaccounted for. In order to provide smooth transitioning between images, interpolation is used.

With the transducer oriented horizontally, circular scanning of the transducer generates a planar image of the transverse cross-section. The data set is redundant with each point in the leg imaged multiple times at the different angles. The advantages provided by this method of scanning are many. Since each anatomical location within the leg is imaged multiple times, image processing algorithms can be used to optimize the image based on the data. Consequently, the image with the most detail can be generated where each pixel within that image has been optimized for brightness and clarity. The resulting images from this technique can be used for diagnostic imaging that is comparable to the resolution of x-ray computed tomography. In fact, because ultrasound is better suited for soft tissue definition than is x-ray, ultrasound images demonstrate clearer tissue interfaces. Volumetric image sets can be generated from horizontal scans by swiping the transducer vertically.

The preferred ultrasound image acquisition system consists of Motorola 68030 based CPU, or the like, video frame grabber, motor controller, and an additional memory board, all housed in a VME bus based enclosure. A Sun-based graphical user interface (GUI), or the like, is used for command and control of the entire system.

Utilizing the GUI, the operator can select the number of images to acquire from the ultrasound machine, choose the start and stop position of the scanner, as well as several other variables for correct operation of the system. Images can also be selected at constant or variable spaced intervals about the subject's leg.

The VME CPU performs the following functions:
a) Reads the command from the operator and calculates the correct rotation rate for the scanner;
b) Commands the scanner to start rotating;
c) Continuously monitors the position of the scanner to decide when to grab the next ultrasound image;
d) Grabs an image and stores it in memory; and
e) On command from operator all images are transferred via Ethernet to host computer when operation is complete for post processing and image reconstruction.

At the present time the output image data from most ultrasound machines is in analog format, and therefore must be digitized. It would be advantageous to obtain the data at the digital level, prior to image processing and output the video image.

Image capturing and scan speed preferably are synchronized to a seven (7) Hertz image frame rate. This signal can be incorporated into the system.

Ultrasound is most accurate when the beam is incident normal to the surface of the subject. As the angle between the transducer and the surface normal increases, image quality rapidly drops off due to reduced pixel intensity and inaccurate distance representation.

The image quality of a leg is best when the incident angle is between +/− ten (10) degrees as the intensity values in the bone and skin images drop noticeably at larger angles. Image quality is best when ultrasound incident angles are between +/− ten (10), and inaccuracies in distance representations in the images occur with incident angles greater than +/− twenty (20).

Figure 3:
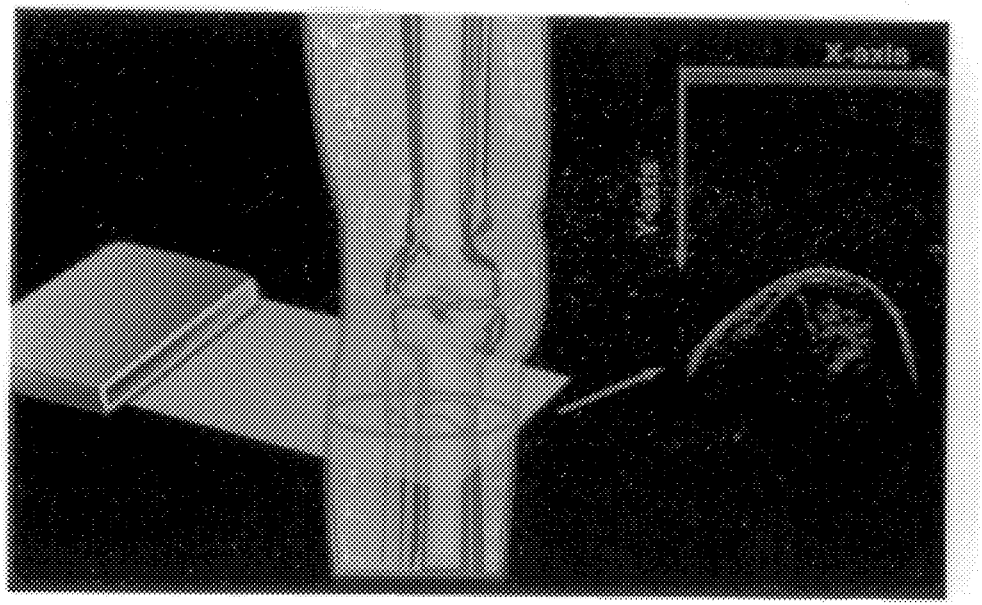
FIG. 3 depicts a typical horizontal reconstruction.

The preferred prosthesis limb scanning apparatuses and methods acquire ultrasonic images in two modes: horizontal and vertical. In the horizontal scanning mode, individual frames are acquired at a predetermined angular increment about the limb, as depicted in FIG. 3. A cross-sectional reconstruction process is then applied which involves angular rotations, motion compensation, and rank filtering, resulting in a highly defined planar cross section of the limb.

Figure 4:
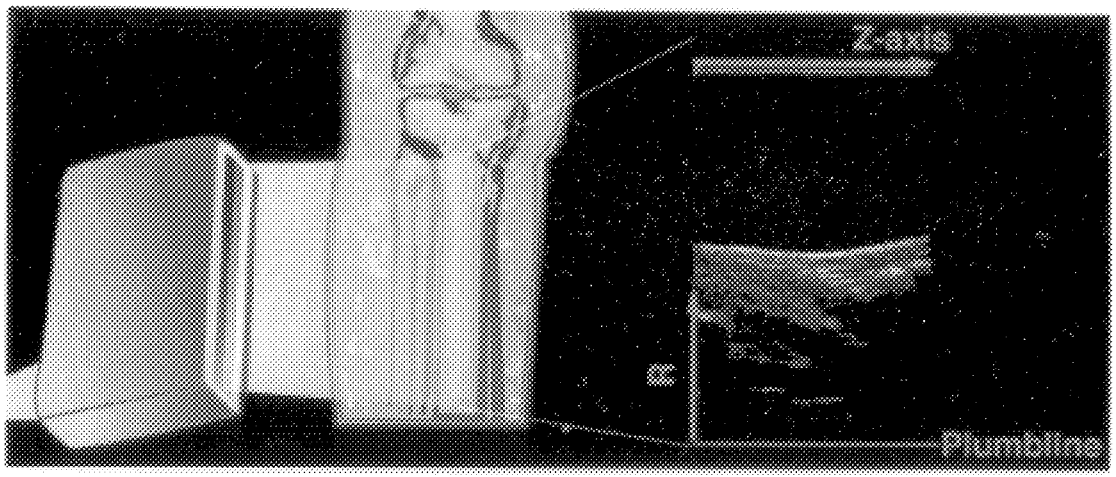
FIG. 4 depicts a typical vertical scanning mode.

In the vertical scanning mode, the transducer is oriented parallel to the vertical axis of the tank. Individual frames are acquired at a predetermined angular increment about the limb, as is seen in FIG. 4. A reconstruction process is then applied which involves angular rotations and polar interpolation, resulting in a volumetric reconstruction. The image and signal processing software developed for processing ultrasonic images can been integrated into the Khoros system, which is an algorithmic development and visualization environment.

In the horizontal scanning mode, the linear transducer is oriented parallel to the bottom of the tank. In this mode, the x axis corresponds to the coordinate axis along the face of the transducer (or cross range), the y axis corresponds to the depth of penetration, or the direction along which sound travels into the tank (or range), and e corresponds to the clockwise angle of the acquired frame with respect to the top, or front, of the limb. See FIG. 3.

In this mode, a mechanical scanning system rotates the ultrasonic transducer about the limb. During the scanning process, individual ultrasonic frames are digitized along with the angle ($\Theta$) of the acquired frame. The reconstruction process involves rotating the individual frames about the center of the trunk. In this reconstruction process individually captured images are rotated with respect to the initial coordinate frame, and all frames are co-registered and combined to generate a composite image. It can be seen from the scanning geometry (FIG. 3) that an individual point within the limb will be visible to the transducer as the transducer sweeps through an angular spread.

For prosthesis fitting, the points of interest are the surfaces of the tibia, fibula, and skin. Both bone and skin in ultrasound data show up as relatively strong signal echoes. Exploiting the redundancy in the data, the maximum signal echo can be chosen from all those signal echoes corresponding to any given point within the limb. The resultant cross section reconstruction seen in FIG. 5 emphasizes the strong signal echoes of the skin and bone, but at the cost of also emphasizing any noise in the system, such as the tank noise around the limb.

The noise signal echoes (tank reflections, bubbles etc.) are not coherent additions to the signal. Instead, the ultrasonic limb signal echoes replace noise signal echoes when present. The preferred technique under these circumstances is to use a rank value filter that employs a percentage ranking of the frames (instead of the average value over N frames) which preserves the desirable signal echoes (of the limb) while it eliminates the undesirable signal echoes (from the tank noise). Using the technique, FIG. 5 (the maximum signal echo) represents the 100% ranking. In using this technique applied to the data set corresponding to that in FIG. 5 and choosing the 90% ranking, it produces the reconstruction shown in FIG. 6.

Figure 6:
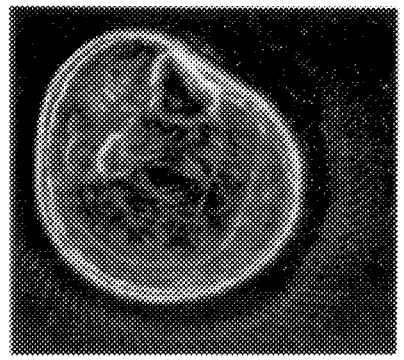
FIG. 6 depicts a typical horizontal rank value filtering construction.
Figure 7:
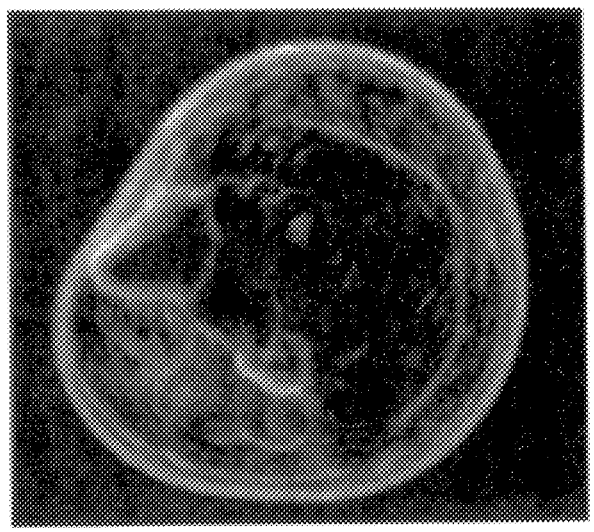
FIG. 7 depicts a typical masked reconstruction.
Figure 8:
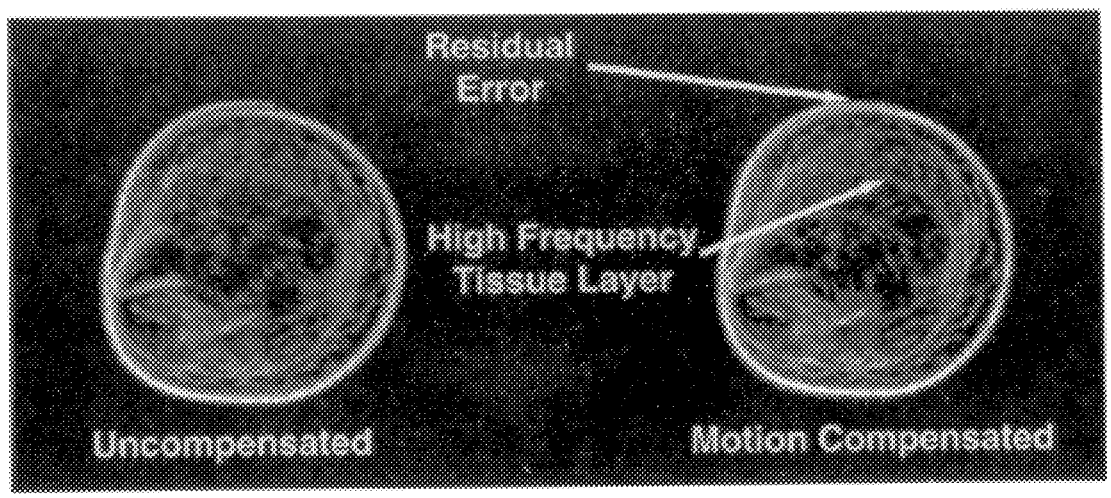

Further, using the non-zero values of the reconstruction in FIG. 6 as a mask to the reconstruction shown in FIG. 5 produces the masked reconstruction shown in FIG. 7. This combination simplifies the task of recognizing the skin and bone signal echoes from within the reconstructed images because it maximizes the signal strength of the skin and bone surfaces while reducing noise.

Figure 8:
FIG. 8 is a comparison of before and after motion compensated images.

A horizontal scan that is generated between forty (40) and one hundred eighty (180) frames will typically require 10–30 seconds to complete. Even during this short period of time patient motion can cause discontinuities in the reconstructed image. Any mechanical method to constrain the motion of the limb will distort the unloaded skin surface. Consequently, a small amount of motion during the scan should be expected. Any motion during the scan will manifest itself as a blur in the reconstructed image, thus adversely affecting the overall image. Depending on the angular increment of successive frames of the acquisition (typically four (4) degrees), the majority of the information results from the same geometry within the limb. Because of this redundant information from frame to frame the data are highly correlated. Any motion of the limb between the acquisition of two frames will result in a shift of the correlation peak of the two frames with respect to each other corresponding to the amount of relative motion. The compensation for such motion is shown in FIG. 8.

In the motion-compensated reconstruction image (FIG. 9), the error has been reduced but not eliminated. This is a result of the integrated residual error over the entire scan. In the motion-compensated reconstruction, the more high spatial frequency information of the structure of the internals of the limb is present.

At first order, the ultrasonic signal echoes of a limb typically exhibit either reflective (specular) or volumetric scattering characteristics. Any given tissue type (bone, skin, muscle layers, etc.) is usually dominated by one of the characteristic types. Specular signal echoes usually fall off quickly with changes in angles of incidence as compared to scattering signal echoes. During an acquisition scan, a two dimensional angle of incidence (versus signal echo value) can be generated for each point within the reconstructed image. Then, the angular dependency of a given point within the limb can be determined. Then, a classifier can be designed to recognize the differences in tissue type based on their angular dependency.

Figure 9:
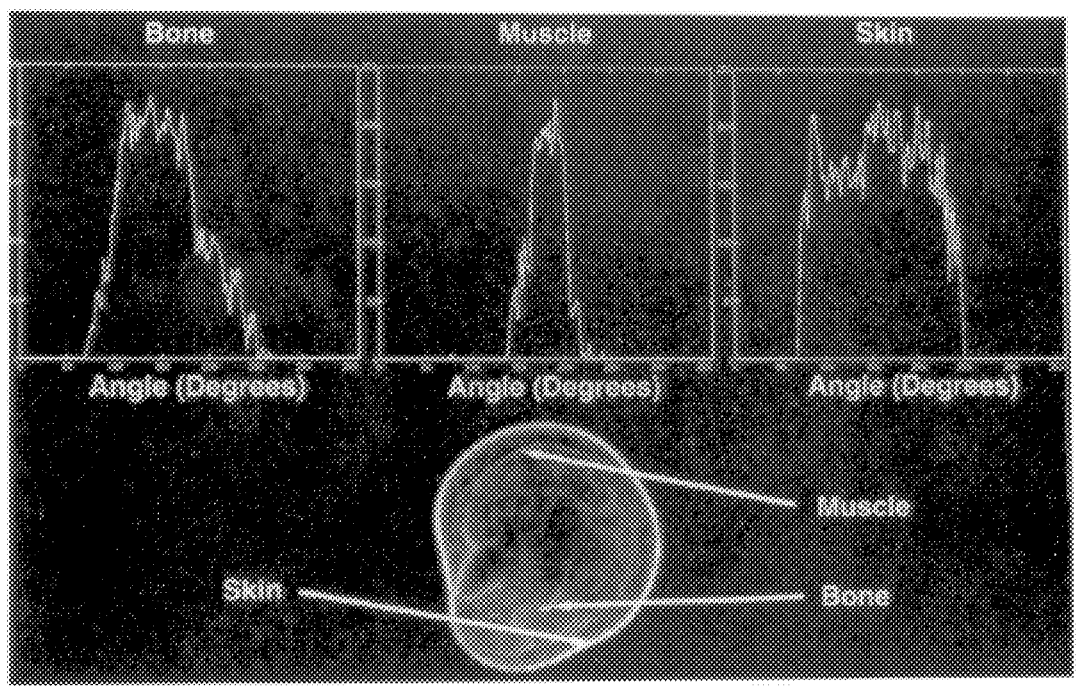
FIG. 9 graphically show the angular dependency of skin, bone and muscle layers.

From within the reconstructed image in FIG. 9, three points can be selected which correspond to a skin signal echo, bone signal echo, and a muscle layer signal echo. The plots exhibit the angular dependencies of these three tissue types. Notice the specular nature of both the muscle and bone, while the skin is much more scattering in nature.

In the vertical scanning mode, the transducer is oriented parallel to the vertical axis of the tank. In this mode, the z axis corresponds to the individual ultrasonic transducer number (or height, increasing going up the limb), the r axis corresponds to the radius from the center (plumb line) of the tank, and $\Theta$ corresponds to the clockwise angle of the acquired frame with respect to the top or front of the limb. See FIG. 4.

A mechanical scanning system rotates the ultrasonic transducer about the limb. During this process, individual ultrasonic frames are digitized along with the angle $\Theta$ of the acquired frame. The reconstruction process involves rotating the individual frames about the center of the tank. This process produces a series of frames which represent the ultrasonic signal echoes of the limb as the transducer is rotated about the limb. By contrast to the horizontally oriented transducer, where redundant information exists from frame to frame, individual points within the limb are observed only once during the scan, and some parts will not ever be visible to the transducer. See FIG. 4.

A bilinear interpolation scheme is employed to produce a volumetric reconstruction of the limb. The bilinear interpolation is carried out for a given z (height) value, which corresponds to a cross sectional plane of the reconstructed limb. The acquired data are presented in polar coordinates, but it is desirable to perform the reconstruction in Cartesian coordinates. Consequently, a polar to Cartesian transformation is performed on the acquired data. For each point in the reconstructed plane, the four "surrounding" points from the acquired data are determined. A bilinear interpolation is performed to determine the value of the reconstructed point. The result is a "stack" of reconstructed cross sections of the limb, one corresponding to each z (height) value. See FIG. 10.

Figure 10:
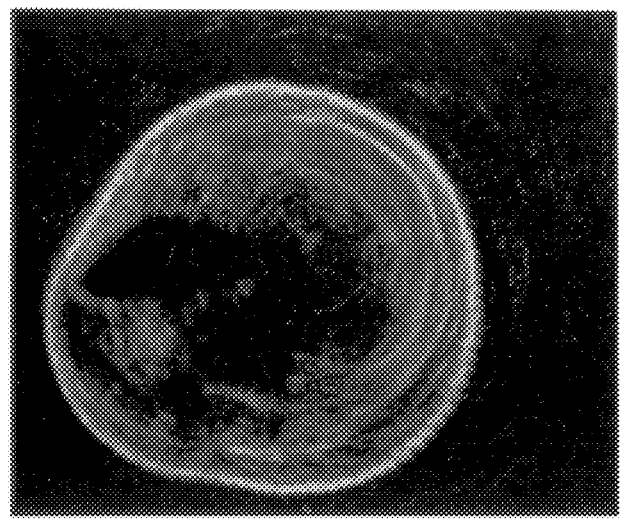
FIG. 10 shows one slice of a vertical reconstruction.
Figure 11:
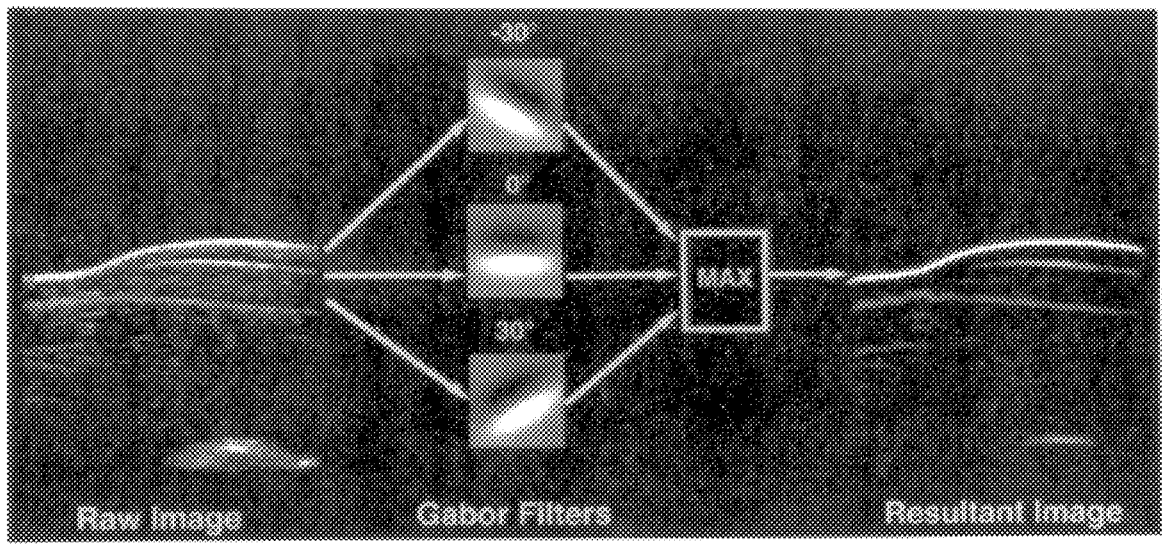
FIG. 11 illustrates the preferred skin recognition process.

An individual frame from a vertical acquisition is shown in FIG. 10. This image corresponds to a vertical slice through the limb. The skin is recognized by correlating set of gabor filters, oriented at −30, 0 and +30 degrees, with the individual frame and determining the maximum response to the set of filters. See FIG. 10. The size of the gabor kernels is determined by heuristic examination of ultrasonic skin signal echoes. The leading edge of the skin response can then determined from heuristic examination of responses to the gabor filters. See FIG. 11.

Figure 12:
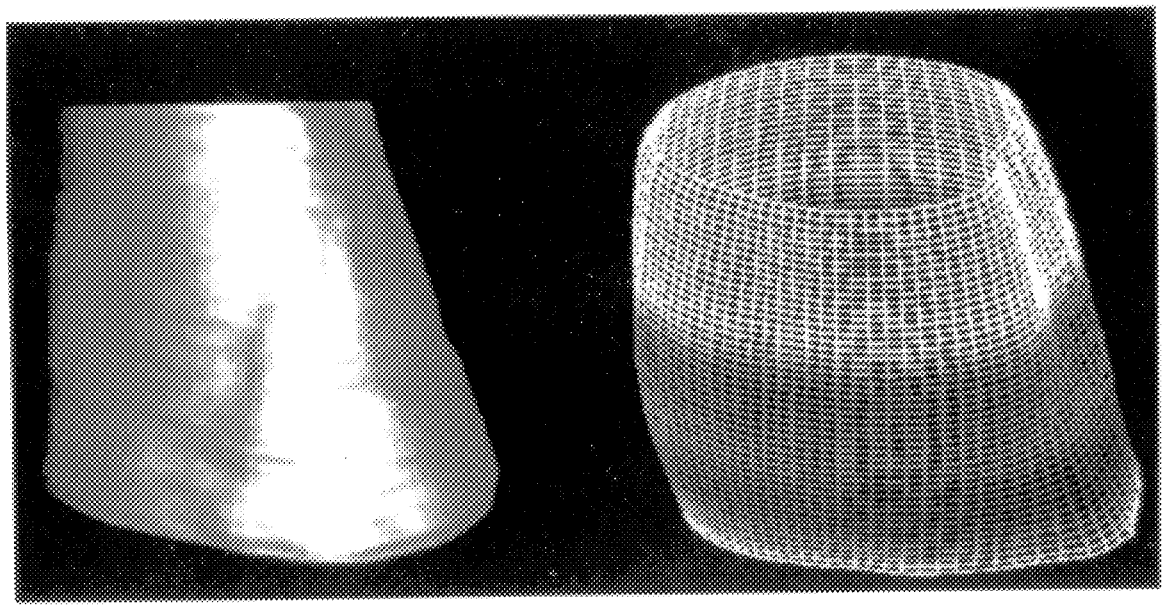
FIG. 12 depicts a typical 3D CAD mesh and visual rendering of a composite image.

The skin locations are recorded in the form r, z, Θ. These sets of points give rise to an overall three dimensional (3D) description of the skin surface of the limb. This 3D description can be entered into a CAD package for potential fabrication of a prosthesis, or any 3D rendering package. See FIG. 12.

Image processing operations can be performed within Khoros, which provides an environment for image processing algorithm exploration with industry standard routines for basic image conversion, processing, and display. Application-specific routines can be integrated into the Khoros system. They may contain calls to standard Khoros library functions or user written library functions that add new functionality to the system.

A Visual Programming Environment (VPE) is also provided that allows Khoros users to direct inputs through a series of these library functions and display the results. With Khoros, a new algorithm can be rapidly prototyped and handed off to image analysts for review. The VPE can also be used by the image analyst for production work. Nine ultrasound specific application routines can be utilized and integrated into the Khoros system. These routines include:

gabor—a routine used to generate a kernel containing a gabor function. The kernel can have arbitrary orientation and size. The Gabor program can generate both even and odd gabor functions.

ncorr—will calculate the normalized correlation of a kernel with an input image. The resulting image will be the extent of the input image. Normalized correlation is only calculated for those positions in which the kernel fits entirely within the input image. Edge effects are not handled.

us2viff—"Ultrasound to Visualization Image File Format (VIFF)" conversion—us2viff takes the raw individual ultrasound frames in conjunction with the acquisition header information (sensor orientation, acquisition angle, date, time, subject, machine characteristics) and produces a multiband VIFF image file. The individual frames are stored as bands in the multiband image.

ush2dxs—"Ultrasound horizontal two dimensional cross section generation" —ush2dxs rotates the individual frames about the plumb line to the angle which corresponds to the actual acquisition; compensates motion between the individual frames; and determines the maximum response throughout the frames on a pixel by pixel basis to produce a composite cross sectional ultrasonic image.

ushmocomp—is used to compensate the individual ultrasound frames for motion of the limbs between successive frames. It exploits the highly correlated nature of successive frames and determines the amount of motion by the shift in the correlation peak.

ushplumb—is a calibration verification tool which will recognize the signal echo of a plumbob within the ultrasound imagery to verify the proper orientation of the sensor with respect to the center of the tank. Statistics are generated for both leading edge and maximum point signal echoes of the plumbob.

ushrank—"Ultrasound horizontal rank value cross sections generation"—rotates the individual frames about the plumb line to the angle which corresponds to the actual acquisition; motion compensates motion; and ranks, across all frames, the individual pixel values to produce a set of ranked cross sections. These cross sections can be chosen to filter out incoherent noise, or other undesirable signal echoes.

usv3dxs—"Ultrasound vertical three dimensional volumetric reconstruction"—rotates (about the plumb line) the individual frames to the angle which corresponds to the actual acquisition; performs polar to Cartesian coordinate system transformation, and then executes a bilinear interpolation scheme to produce a series of two dimensional cross sections. The resulting "stack" of two dimensional cross sections is then assembled to produce an overall volumetric reconstruction of the limb.

usvskin—uses the individual vertically scanned frames to create a 3D description of the skin surface. The skin is recognized by applying a set of gabor filters to the individual frames and determining the maximum response to the set of filters. The skin location or leading edge of the skin response is saved in the form r, z, Θ). These sets of points give rise to an overall 3D description of the skin surface of the limb.

Figure 13:
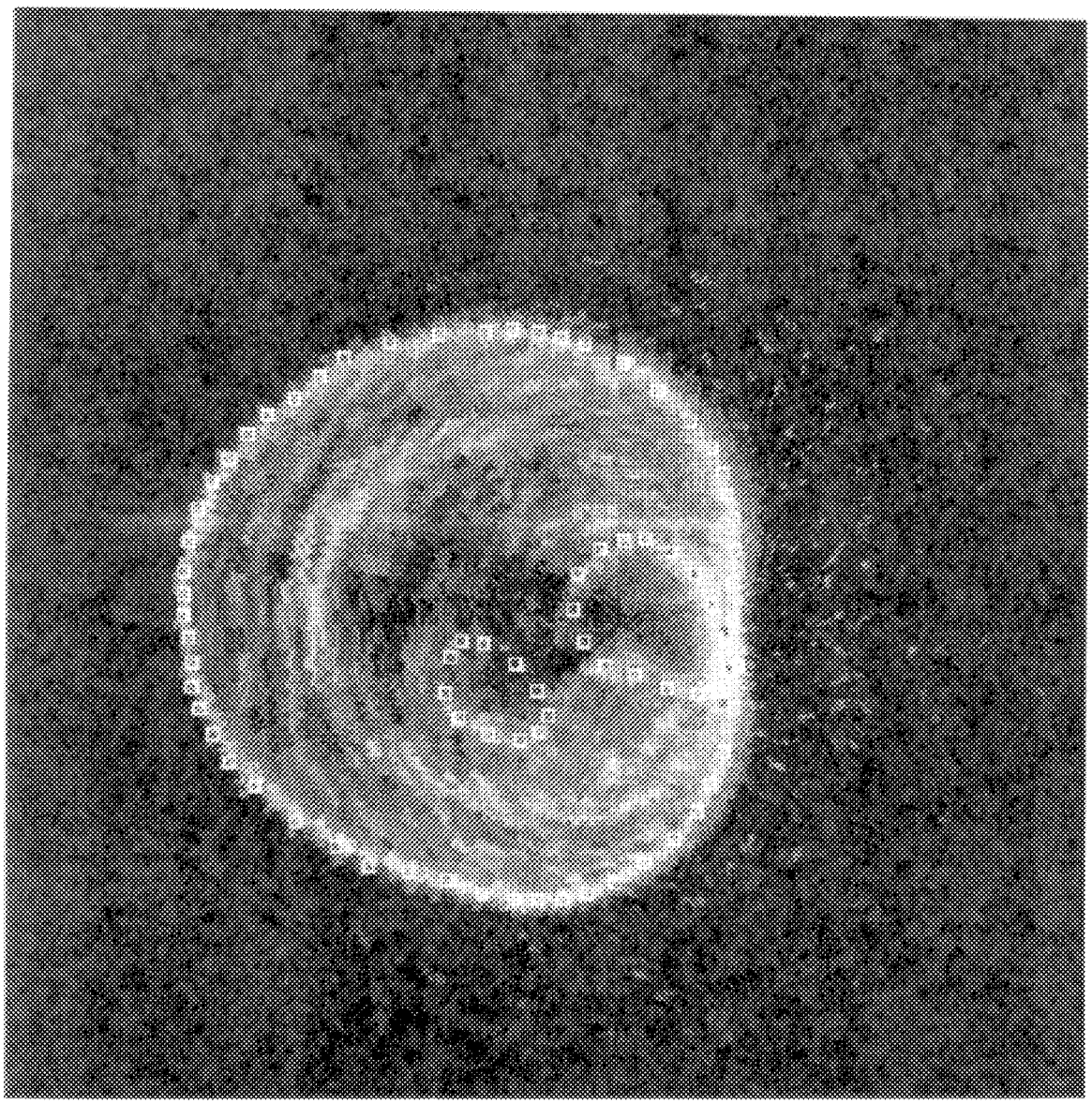
FIG. 13 is an example of segmented image with a user interface.

Skin and bone surface segmentation can be performed from vertical scans with a flexible, interactive program that displays horizontal cut images made from the vertical scans. The program works on one cut at a time. The user begins the segmentation by providing an initial approximation on one cut. An automated segmentation program then takes over to refine the initial approximation. The final result is a file of three dimensional points made up of all the cuts. An example of a segmented image with the user interface is shown in FIG. 13.

The user provides initial approximations of discrete contour points that give a rough outline of the skin and two bones. The graphical user interface displays the image data and gives mouse-driven, or the like, controls for making these approximations. To approximate the outline of the skin, the user sets a gray-level threshold that separates the darker image background from the brighter pixels on the skin. A radial line is traced from the outer edge of the image toward the center. The first skin point is taken at the place where this line first crosses the threshold. Starting from this point, the program traces the remainder of the skin by looking for nearby above-threshold values. The two bone contours come from pre-stored, approximate outlines of typical bones consisting of about 20 points each. The user drags these contours to the approximately correct location on the image. The program allows the user to rotate and scale all the contours and to move individual points of the contours.

These initial approximations serve as the starting point for the automatic segmentation program. This program refines the discrete contour points to make them fall precisely on the bright ridges in the image. The automatic segmentation program uses active contours called "snakes". Snakes work by solving an energy minimization problem for each contour. The "energy" is a sum of the (negative) pixel brightness along the contour and the bending energy of the contour. The bending energy is proportional to a weighted sum of the first and second derivatives along the contour. The positions of the contour points are iteratively moved to minimize the total energy. The brightness term tends to move the points toward image maxima, while the bending terms tend to keep the contour smooth. Together, these terms make the contour track bright ridges in the image while remaining smooth through gaps and noise.

Figure 14:
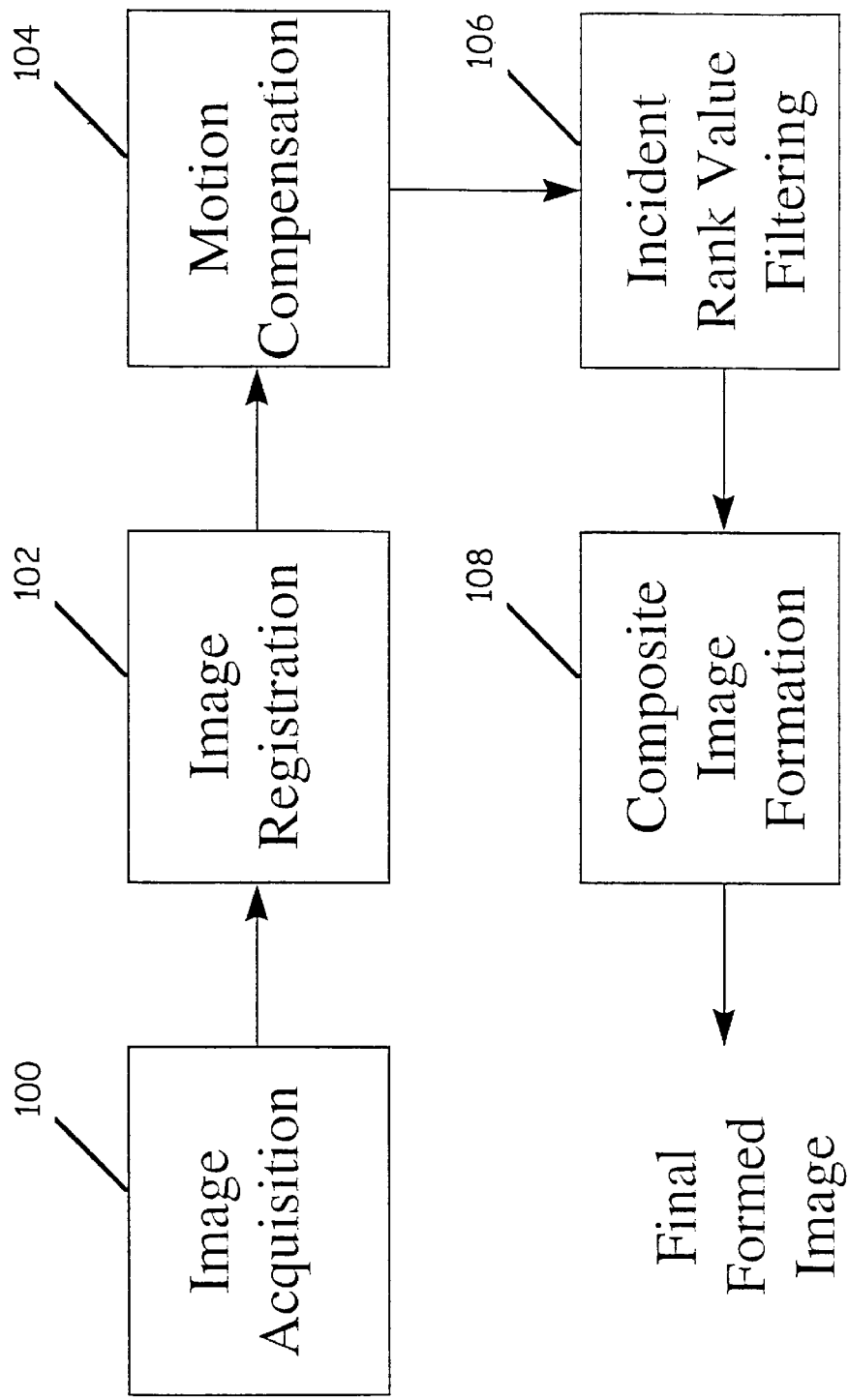
FIG. 14 is a block diagram of the preferred 2D horizontal scanning mode.

Image processing in the horizontal scanning mode is depicted in FIG. 14. Individual ultrasonic frames are acquired at a predetermined angular increment about the scanned object (in this case a lower human limb). A cross-sectional reconstruction process is then applied which involves image acquisition 100, image registration 102, motion compensation 104, incident rank value filtering 106 and composite image formation 108.

Figure 15:
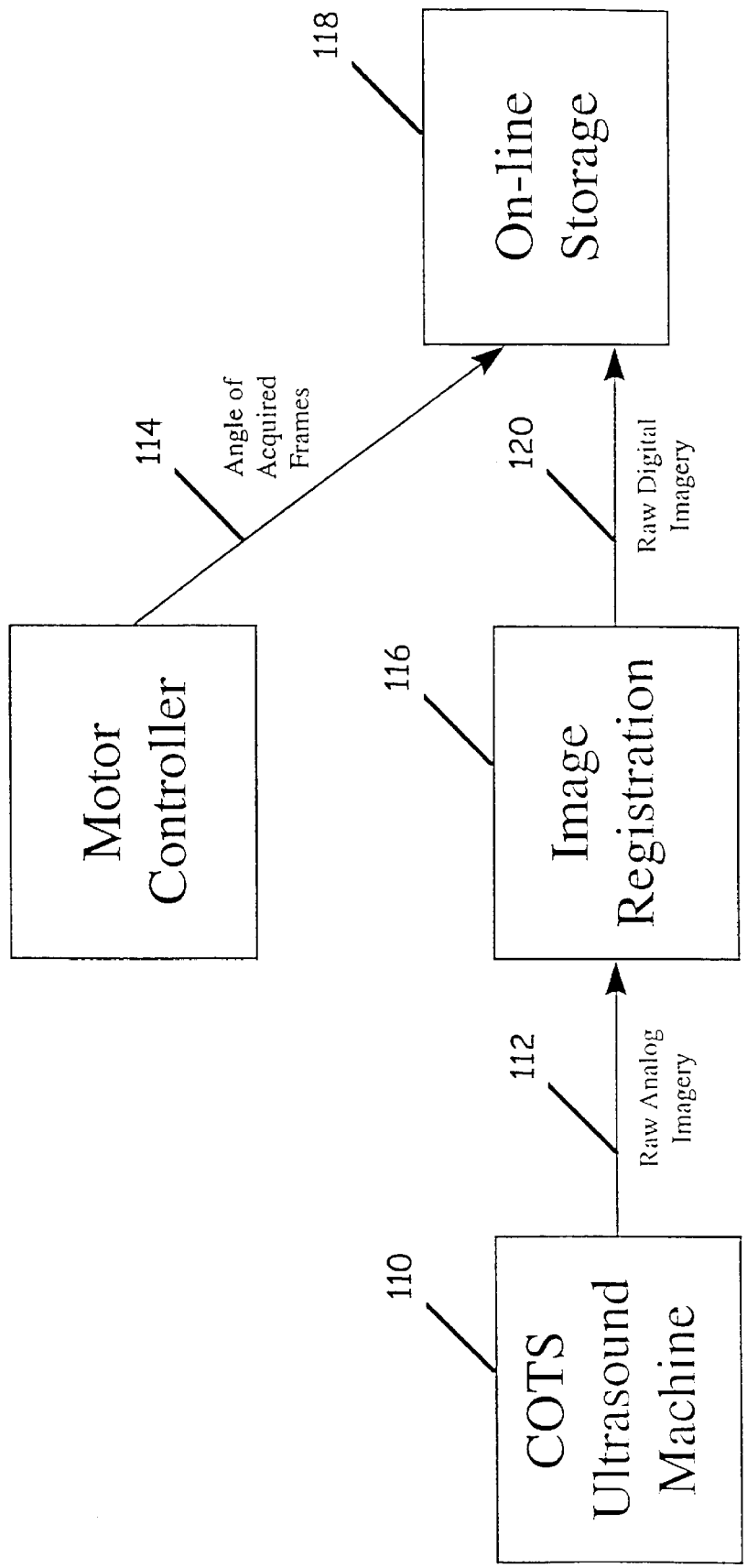
FIG. 15 is a block diagram of the preferred 2D horizontal image acquisition structure.

The image acquisition process and structure as shown in FIG. 15, comprise a commercial off-the-shelf (COTS) ultrasound machine 110. A linear ultrasonic transducer is oriented parallel to the bottom of the tank and transverse to the scanned object. In this mode, the x axis corresponds to the coordinate axis along the face of the transducer (or cross range), the y axis corresponds to the depth of penetration, or the direction along which sound travels into the tank (or range), and theta corresponds to the clockwise angle of the acquired frame with respect to the top, or front, of the scanned object.

In this mode, a mechanical scanning system rotates the ultrasonic transducer about the scanned object. The ultrasound machine produces raw analog imagery 112 (RS170, video) while the mechanical scanning system produces a digital signal 114 containing the clockwise angle of the acquired frame. A computer system configured with a video frame grabber 116 is then used to digitize the ultrasonic raw frames 120 and record the digital signal containing the angle of the acquired frame. The ultrasonic raw frames and angles of acquired frames are then moved to the system's on-line storage 118.

Figure 16:
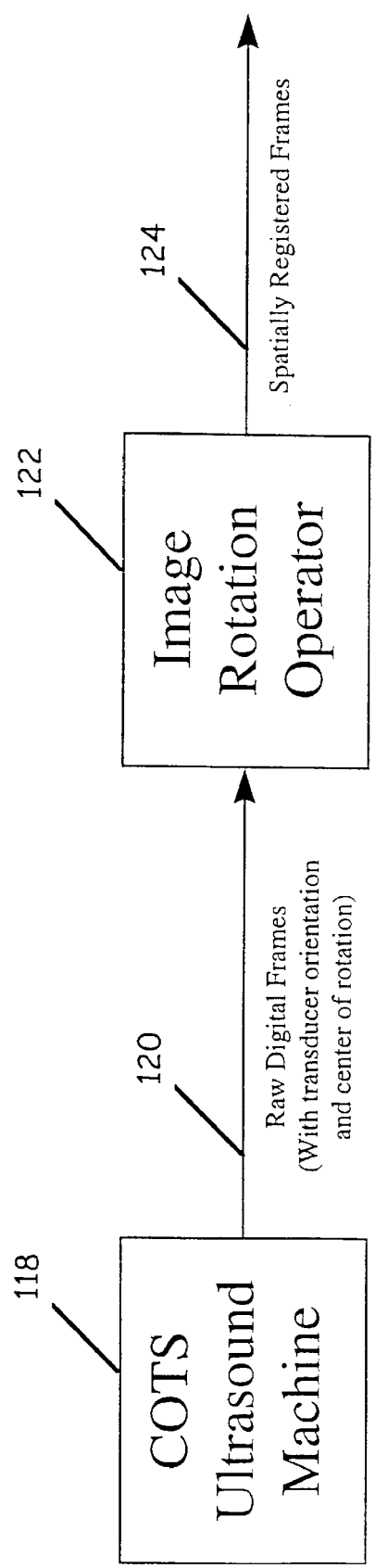
FIG. 16 is a block diagram of the preferred 2D horizontal image registration structure.

Image registration is shown in FIG. 16. From on-line storage 118, ultrasonic raw digital frames 120, along with the transducer orientation and the center of rotation, are used in a image rotation operation 122. Using the center of rotation and the transducer orientation, the ultrasonic frames are rotated about the center of rotation to the angle at which they were acquired. The resultant frames are spatially registered 124.

Figure 17:
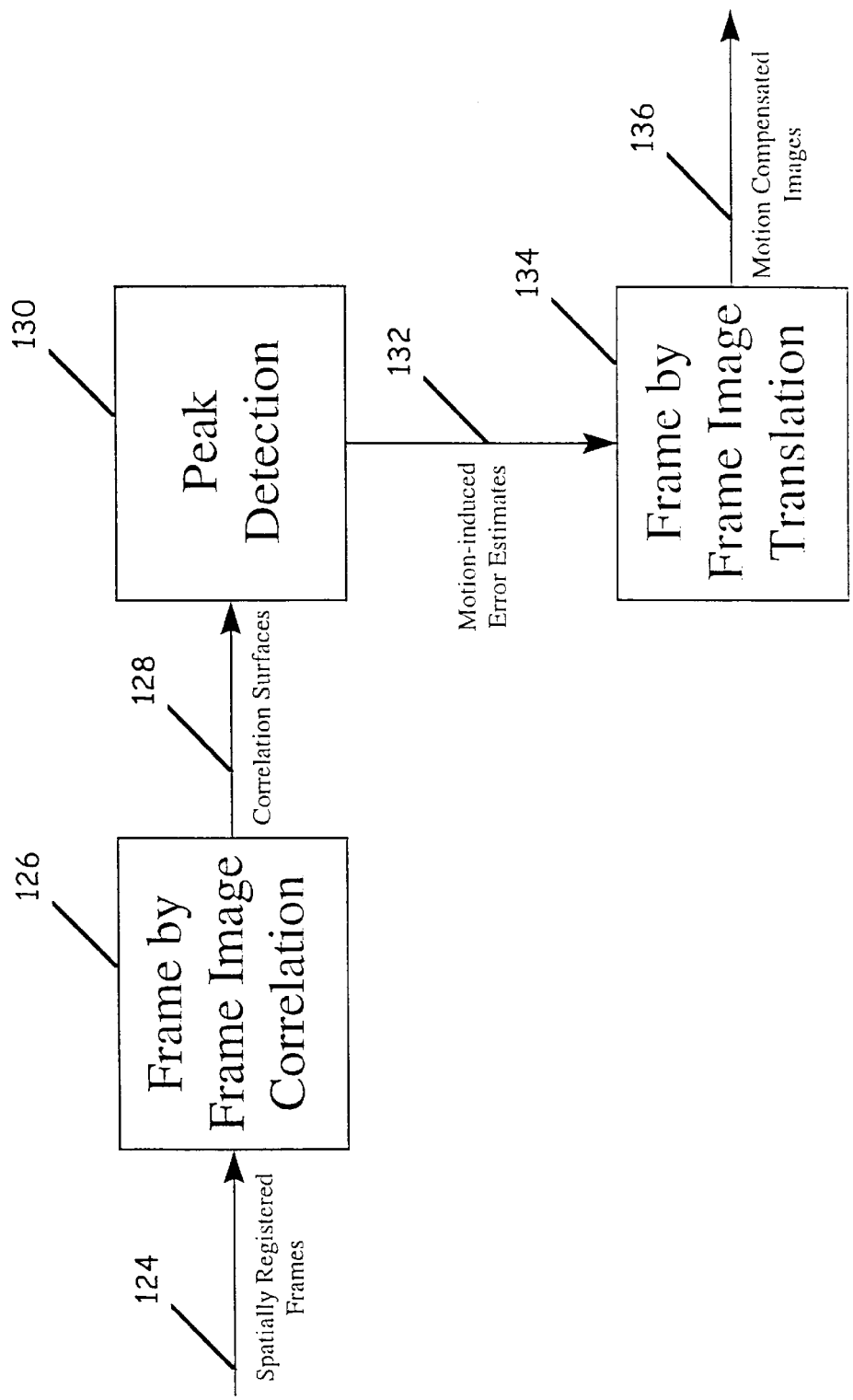
FIG. 17 is a block diagram of the preferred 2D horizontal image motion compensation structure.

The motion compensation process is shown in FIG. 17. During the image acquisition phase, any motion of the scanned object will manifest itself by a blurring in the reconstructed cross section. It is desirable to sense and compensate for such motion. Depending on the angular increment of successive spatially registered frames 124 of the acquisition, the majority of the information results from the same geometry within the scanned object. Because of the common information from frame to frame, the data are highly correlated. A frame by frame image correlation 126 operation is applied resulting in correlation surfaces 128. For each surface, a peak value (or greatest value) is detected 130. The amount the peak is shifted from the center of the correlation surface gives rise to a motion-induced error estimate 132 (translation error). These motion-induced error estimates 132 are applied in the form of frame by frame translations 134 to produce motion compensated images 136.

Figure 18:
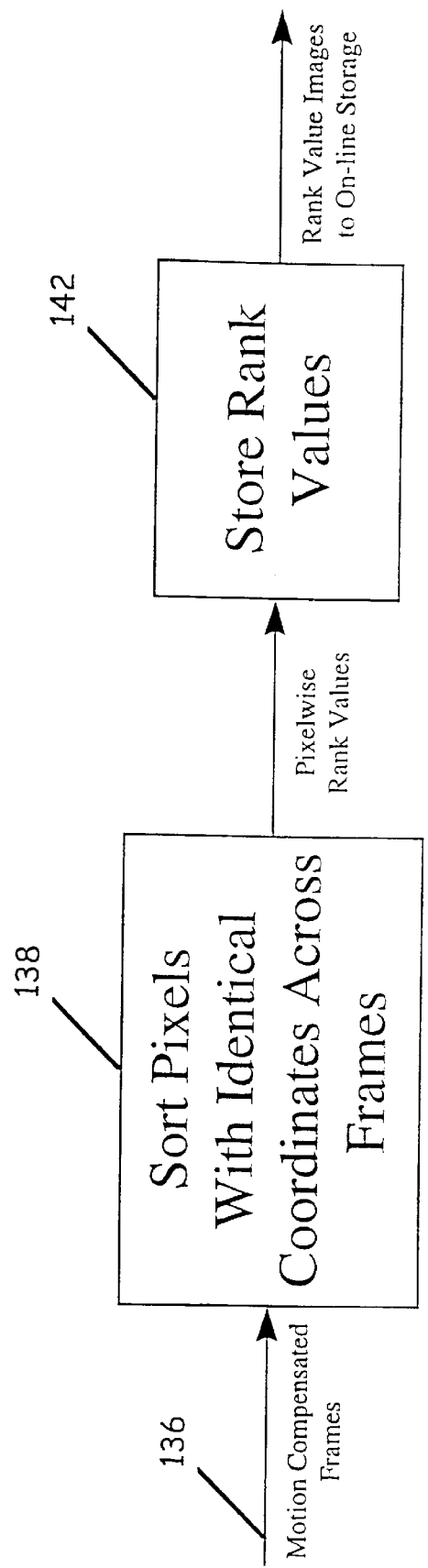
FIG. 18 is a block diagram of the preferred 2D horizontal image incident rank filtering process.

The incident rank value filtering process is shown in FIG. 18. Within the motion compensated frames 136, an individual pixel in the acquired geometry (within the scanned object) will be repeated in a number of frames. Rank value filtering is applied by sorting the pixels within the scanned object with identical coordinates across all frames 138. The rank value images, sorted from minimum to maximum, are then stored 142.

Figure 19:
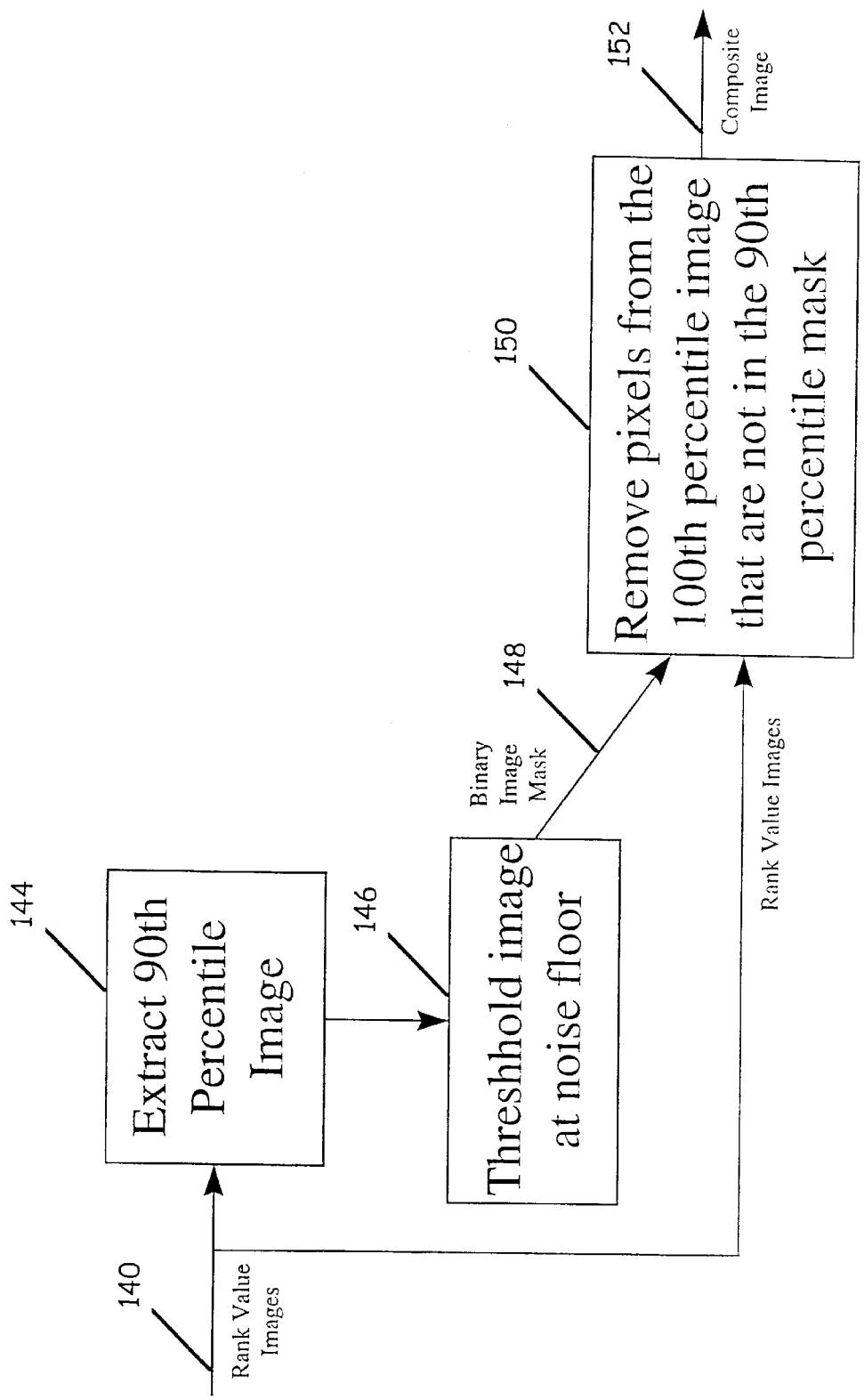
FIG. 19 is a block diagram of the preferred 2D horizontal image composite image formation process.

To produce the final composite image as shown in FIG. 19, first the 90th percentile image is extracted 144 from the rank value images 140 (with 100th percentile being the greatest value). The 90th extracted image 144 is then threshold at the noise floor 146 of the ultrasound machine. This produces a binary image mask 148 with values of zero where the 90th percentile image was at or below the noise floor and one where the image was above the noise floor. An image is constructed from the pixels in the 100th percentile image that are in the 90th percentile mask image 150 (with value of one). The final composite image 152 that is formed is motion compensated and noise suppressed.

For tissue classification as shown in FIG. 9, in the first order, the ultrasonic signal echoes of the human anatomy typically are described by either reflective (specular) or volumetric scattering characteristics. Any given tissue type such as bone, skin, blood vessels, muscle layers layers etc. is usually dominated by one of the characteristic types. Specular signal echoes usually diminish quickly with changes in angles of incidence when compared to scattering signal echoes.

A typical 2D horizontal mode process involves the following steps: 1) An angle of incidence, as compared to a signal echo value, is generated for each pixel within the scanned geometry; 2) The angular dependency of a given pixel within the scanned object is determined; and 3) a classifier recognizes the differences in tissue types based on their angular dependency. This is of particular importance when the above techniques are expanded to use in imaging abdominal cavities and other parts of the human anatomy.

Figure 20:
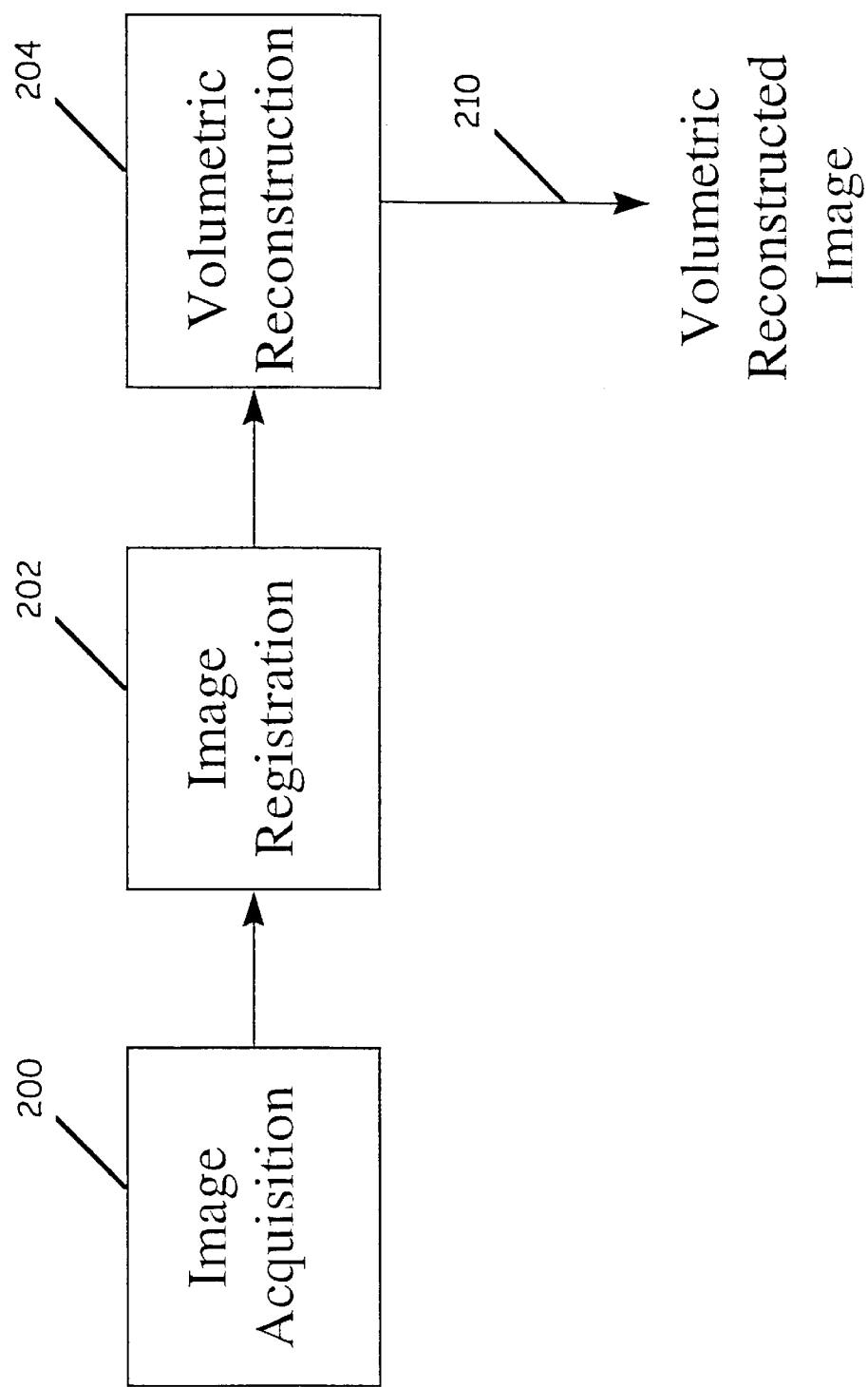
FIG. 20 is a block diagram of the preferred 3D vertical mode functional overview.

FIG. 20 depicts the preferred 3D-vertical mode functional overview. In the vertical scanning mode, individual ultrasonic frames are acquired at a predetermined angular increment about the scanned object (in this case a lower human limb). A 3D volumetric reconstruction process is then applied which involves image acquisition 200, image registration 202 and vertical reconstruction 204.

The image acquisition process and apparatus is similar to the 2D system in FIG. 15. However, the linear ultrasonic transducer is oriented perpendicular to the bottom of the tank and parallel to the scanned object. In this mode, the z axis corresponds to the individual ultrasonic transducer number, or height (increasing going up), the r axis corresponds to the radius from the center, or plumb line, of the tank, and theta corresponds to the clockwise angle of the acquired frame with respect to the top, or front, of the scanned object as observer from above the tank.

Referring to FIG. 15, in this mode, a mechanical scanning system rotates the ultrasonic transducer about the scanned object. The ultrasound machine 110 produces raw analog imagery 112 (RS170, video) while the mechanical scanning system produces a digital signal containing the clockwise angle of the acquired frame. A computer system configured with a video frame grabber 116 is then used to digitize the ultrasonic raw frames and record the digital signal containing the angle of the acquired frame. The ultrasonic raw frames and angles of acquired frames are then moved to the system's on-line storage 118.

Image registration in the 3D mode is also similar to the 2D system as shown in FIG. 16. From on-line storage 118, the ultrasonic raw digital frames 120, along with the transducer orientation and the center of rotation, are used in a image rotation operation 122. Using the center of rotation and the transducer orientation, the ultrasonic frames are rotated about the center of rotation to the angle at which they were acquired. The resultant frames are spatially registered 124.

Figure 21:
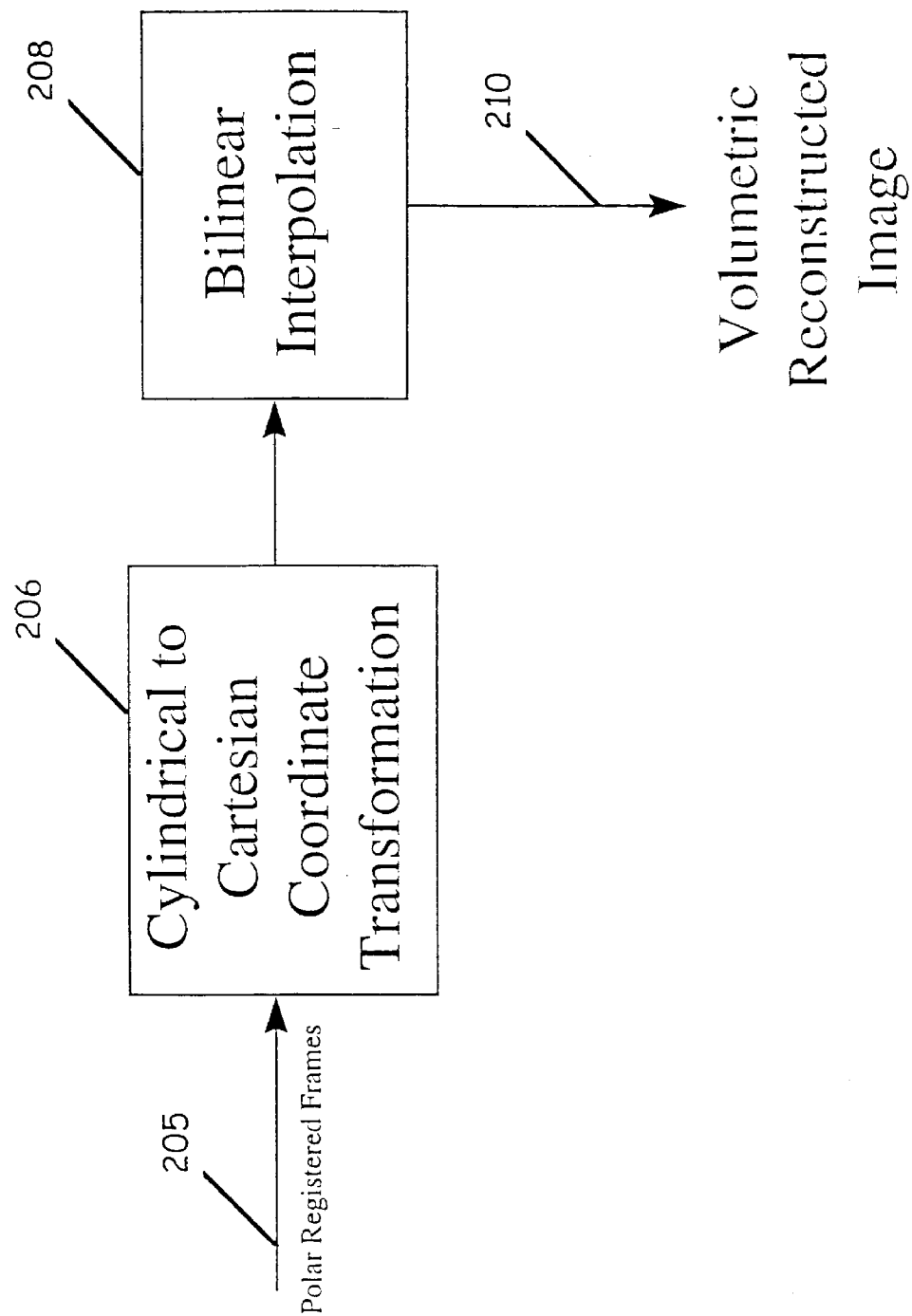
FIG. 21 is a block diagram of the preferred 3D vertical mode vertical reconstruction process.

The vertical reconstruction process is shown in FIG. 21. Polar spatially registered frames 205 are presented in cylidrical coordinates (r,z,theta), but it is desirable to perform the reconstruction in Cartesian coordinates. A cylidrical to Cartesian transformation 206 is performed on the polar registered frames 205 producing a set of Cartesian planes, one corresponding for each individual z value in the acquired data. A bilinear interpolation scheme 208 is employed to produce a volumetric reconstruction 210 of the scanned object. For each point in the individual Cartesian planes, the four "surrounding" points from the acquired data are determined. A bilinear interpolation is performed to determine the value of the reconstructed point. The result is a set of planes of reconstructed cross sections of the scanned object, one corresponding to each z (height) value.

In operation skin recognition is performed by utilizing individual frames from a vertical acquisition which corresponds to a vertical slice through the limb. The skin is recognized by correlating a set of gabor filters against the individual frame. These filters are oriented −30,0 and +30 degrees, and the maximum response from the three filters for each point in the frame is recorded. The leading edge of the skin response is then determined by the brightest pixel observed for a given z value. The z,r and theta for that skin point are recorded. The process is repeated for all values and all acquired frames giving rise to a complete three dimensional description of the surface of the limb. This 3D description can be entered into a CAD package for potential fabrication of a 3D model of the scanned object (limb).

Once the image processing is completed, a digitized composite image can be utilized to fabricate a biomechanically correct prosthesis without reliance on an artisans experience. In the alternative, the digitized composite image can be displayed on a monitor, with the user manipulating the images for use as a diagnostic tool.

Long term clinical research will benefit from the present invention by being able to track the atrophy of residual limbs over time. There has been no method of accurately measuring this phenomenon because suitable data has not been acquired. The soft tissue atrophies with time, but the bone structure remains much the same. Locating the bone structure is necessary to track where the relative changes occur in the soft tissue. If the location of the bone structure can be determined using a non-contact ultrasound imager, then it will be possible to track patients over time using a low cost non-invasive procedure.

In addition to prosthesis fabrication, the present invention can be used as a diagnostic tool for hospital, clinic or field use to replace the present three dimensional diagnostic systems. Present three dimensional imaging systems to not have motion compensation which would discourage use in the field and their expense and physical size is prohibitive for such uses. A portable diagnostic imaging in forward echelon combat areas would greatly benefit army medics to determine the extent of injury and focus care on those wounded that have the highest probability of survival during the first hour of injury. In addition, the system could be made available to emergency medical technicians (EMTs) for civilian work. This information would provide high quality, high resolution, real time, 3-D ultrasound imaging necessary for diagnostics in the field that can be transmitted via telemetry to physicians for a diagnosis for the harmful affects of ionizing radiation that accompany the use of x-rays. The three major contributing factors in successful high resolution ultrasound imaging are optimizing, image acquisition producing redundant data, image processing and image display. The ultrasound system comprises a tracking arm, transducer and coupling medium built into a hand-held device for remote imaging.

Figure 22:
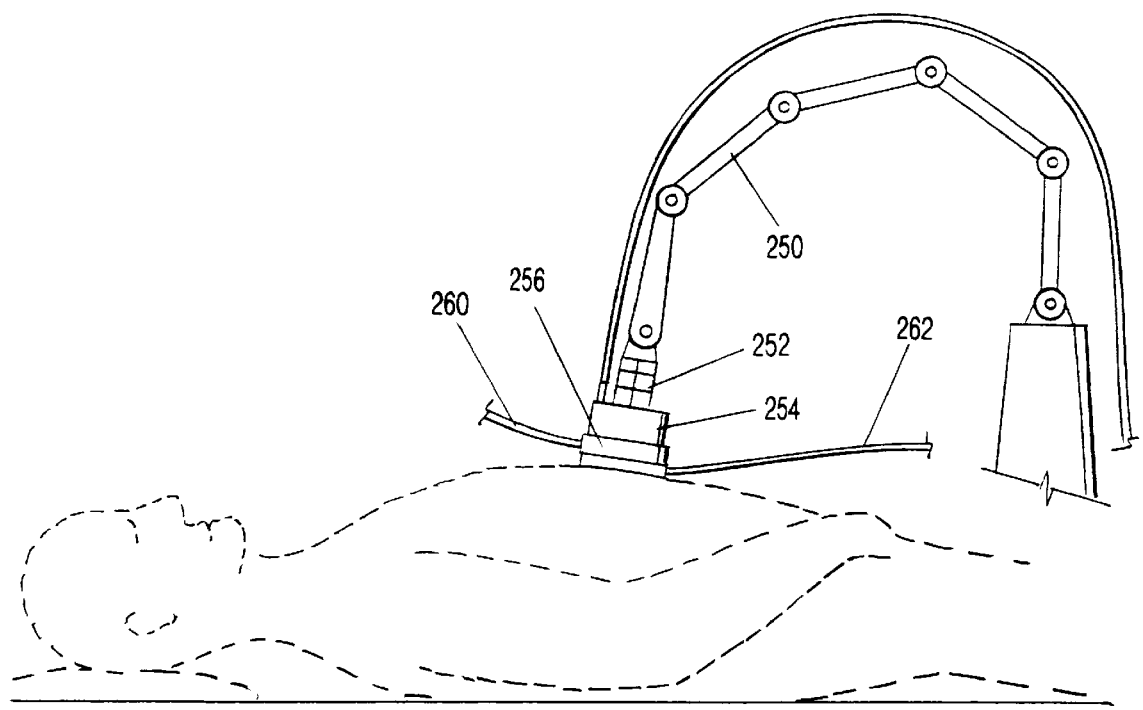
FIG. 22 depicts the preferred ultrasonic diagnostic system.

The preferred ultrasonic diagnostic system is shown in FIG. 22. Similar hardware and software components as described in the prosthesis fabrication embodiment are utilized in this embodiment. A six axis robotic arm 250 is utilized with requisite motors and encoders for position and angle data. Force sensor 252 is attached to robotic arm 250 to monitor and record force data. Ultrasound transducer 254 is attached to coupling 256 as shown. Cup 256 with seal assembly 258 is affixed to ultrasound transducer 254. Water is pumped through cup 256 through water inlet 260 and out through outlet 262.

Robotic arm 250 will help guide transducer 254 via passive or active path overlays to optimize image acquisition thereby maintaining perpendicularity to tissue, acoustic planes and controlling scan path trajectories. Data is processed for transmission with real time hardware. Telemetry transmission to the physician will allow them to further analyze the data or process the data for specific formatting such as two-dimensional cross-sections.

Figure 23:
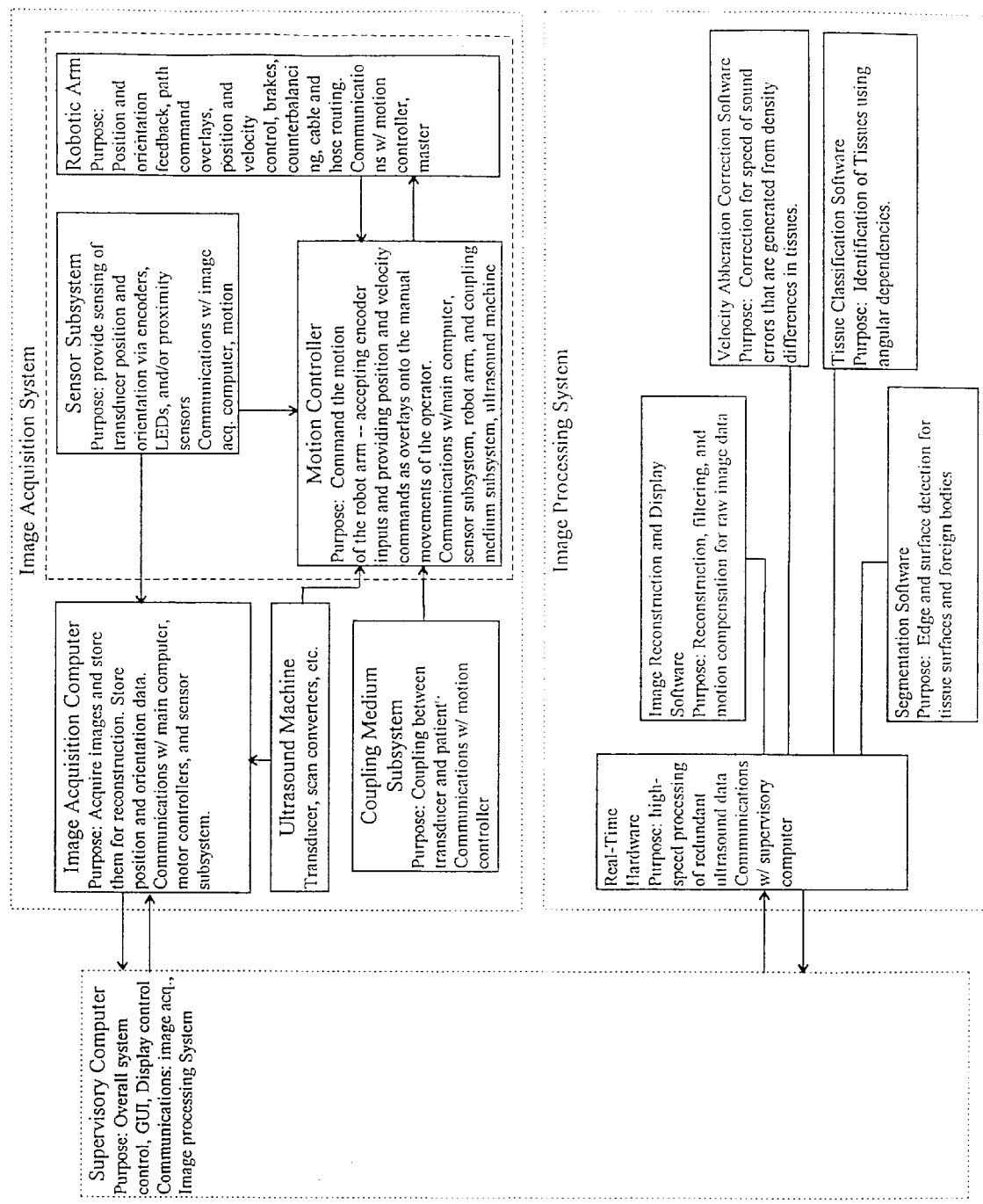
FIG. 23 is a flow chart showing the preferred ultrasonic diagnostic system.

The key elements providing a high quality, portable ultrasound system includes the following: coupling medium paradigm, which include water baths, standoffs, low flow water streams as well as other well known coupling mediums; electro-mechanical arm which allows control of the image acquisition path and includes position and orientation feedback, transducer steering based on computer generated or master input path overlays; support for the transducer cable and water supply lines and counterbalancing; velocity aberration correction based on redundant data; software for path planning of the transducer; real time hardware and software for image acquisition and image processing; image compression hardware and software; telemetry; and image display (2D or 3D, in real time). A flowchart depicting this system is shown in FIG. 23. Since ultrasound requires a coupling medium 300 in order to provide the transmission of an ultrasound signal, preferably water baths is used to act as the coupling agent. Other coupling agents such as stand off pads, gel pads or other known coupling agents in the art can be utilized. A low-flow, sterile, saline stream could be used a coupling medium as well as serving to provide sterile irrigation. Additionally, a water stream could be used to flow over non-penetrated skin surfaces without the need for a large source of water. However, flow rates, bubbles in the stream and fluid volume capacity must be considered. The most important component in obtaining high quality images is the optimization of image acquisition during scanning. A six degree of freedom mechanical arm 250 can be utilized to position and orient end mounted transducer on a standard ultrasound machine 254, and also to provide near perpendicular orientation and path control for redundant data gathering mechanical arm 250 will enable transducer position and orientation data to be available for reconstruction of ultrasound images. This is superior to any non-contact based device because it provides precise information without concerns of obstructive line of sight or metallic interference issues that limit non-contact devices. Mechanical arm 250 can be made compact and can incorporate counterbalancing devices allowing the transducer to be manipulating manually without difficulty. This will allow brakes and/or motors to be incorporated to kinematically control the path, thereby, optimizing the movement for near normal (perpendicular) orientation during motion. Sensors such as reflected light through the water path can be used upon perpendicularity for control adjustments (not shown). Alternatively, a master slave concept could be implemented to provide control of transducer positioning to remote surgeons/physicians. The master, controlled by the home base surgeon could be moved in the direction desired. The slave controlled by the clinician, could be moved by the medic, with brakes or motors providing steering to overlay the desired path. Computer generated overlays can also be used to optimize the path and orientation of the transducer 254 over the body. Mechanical arm 250 will also provide support for cables, the water supply to the transducer as would a cable tray. Robotic simulation software, well known in the art, will be utilized to optimize mechanical arms 250 range motion for applications to various human anatomy. Path finding algorithms can also be employed that provided a model the scan path that should be taken in order to optimize the image acquisition.

The traditional method of image compression for fast transmission is to use a standard image compression algorithm such as JPEG or MPEG. Although these image compression schemes could be employed to optimize the data transmission, it would be beneficial to the physicians if "information triage" is performed prior to viewing. Information triage will take the form of image processing and segmentation to define the location of wound or shrapnel in combination with localized blood flow from Doppler in order to provide "improved" data to the physicians. By performing this image processing prior to viewing, a data compression ratio of over 1000:1 could potentially be accomplished for shrapnel and Doppler related data. Remaining data compression will be accomplished as described below.

Velocity inhomogeneities cause roughly two kinds of distortion in ultrasound images. Small-scale inhomogeneities cause blurred and locally distorted images, and this effect can be reduced with phase aberration correction. The other kind of velocity inhomogeneities are large-scale, and this is a potentially more serious problem than the small-scale type, because they cannot be solved with phase aberration correction. Large-scale inhomogeneities occur when the tissues being imaged have significant differences in their speeds of sound. These differences in velocity cause distortion in the range coordinate (time axis) as well as distortion in the transverse coordinate due to bending or deflection of the rays representing the beam. Consider the example of two homogeneous cubes, one contained in the other. If the propagation velocities are different the image of the embedded cube will be distorted and the distortion will be dependent on transducer/imaging geometry and aspect angle. Thus, large-scale inhomogeneities cause geometric distortions in the image that will affect the accuracy of a medical diagnosis.

The problem of large-scale velocity inhomogeneities can be solved with redundant imaging. By combining many different views of the tissue from multiple directions, one can explicitly detect geometric distortions. Redundant imaging also has the effect of enhancing the image of smooth (specular) objects or interfaces. Small features can be tracked from view to view, looking for size changes attributable to velocity inhomogeneities. This incorporates optical speckle techniques as well as image processing techniques from digital signal processing, radar pattern recognition and morphology.

Phase-aberration correction techniques can be incorporated in the system. These techniques are strongly coupled to the hardware design and require processing of the signal from individual transducer elements. Methods for phase aberration correction can be applied to the linear, complex image that is available from some of the new ultrasound machines such as the General Electric LOGIQ 700.

The present invention can provide redundant imagery from multiple scanning geometries and form images exploiting that redundancy. From the redundant imagery, rudimentary angular reflection and scattering characteristics of various tissue types (skin, bone, muscle layers, etc.) may be extracted. Different tissue types will exhibit varying characteristics, and classification of tissue based on the reflection and scattering properties is possible. Mathematical and statistical foundations to autonomously classify various tissues types and techniques to display, manipulate and visualize the resulting two and three dimensional imagery can be made. The results should enhance the medical expert's ability to provide high quality diagnostic information to the clinician in the field.

High quality diagnostic images from a field portable ultrasonic system should be provided to the rear echelon hospital in near real time to enhance a patient's survival during the first hour following injury.

The time latency associated with the image formation and processing techniques can be reduced by providing a system solution combining Commercial Off-The-Shelf (COTS) hardware and system integration into a standard VME chassis. The image forming and processing techniques are broken down into the basic image and signal processing operations required. The COTS hardware is then selected that maps these basic operations most efficiently. The basic operations include but are not limited to image capture, translation, rotation, spatial filtering, time series filtering, convolution. The resultant system could be integrated into a Medical H for inclusion into an overall real time field portable ultrasonic system.

In the far forward battlefield scenario in which a medically equipped HMMMV would be use for initial medical diagnosis of injuries suffered from conflicts in proximity to the Forward Line Of Troops (FLOT), it may be desirable to provide ultrasonic imagery via satellite link to rear echelon specialists up to hundreds of miles away (or even in the continental United States). Critical is the ultrasonic image compression technology that would allow ultrasonic imagery from two and three dimensional composites produced to be compressed while preserving image quality and integrity. Because of the expense involve in high bandwidth SAT-COM links, it is desired to accomplish image transmission over a Ti data link with bandwidth limitation of 1,500,000 bits per second. This could provide a much broader area of coverage and flexibility of operation.

Ultrasonic and Synthetic Aperture Radar (SAR) imagery are very similar in nature and compression techniques that apply for SAR imagery should performs quite well for ultrasonic imagery. SAR is an army target recognition system. The techniques derived for compression of ultrasonic imagery can also be applied to storage and recall of imagery at rear echelon medical facilities or other central repositories for military medical records.

The most cost-effective and reliable method of transmitting the data from the forward echelon to the rear is to transmit the data in its raw format. This minimizes the equipment and computational power required at the mobile site. In addition, all of the computational hardware is kept in a controlled environment—increasing the reliability of the overall system. The single computational unit can be used to process multiple input sources from multiple sites. Using data compression and approximately 10 frames per second video, the raw data transmission rate can be reduced to between 1–4 Mbits/second. This data transmission rate can be implemented using standard off-the-shelf RF telemetry hardware.

For far forward battlefield applications, portable, real-time hardware will be used to process data. However, in the rear echelon, access to an HPCC could be provided for processing power necessary for CPU-intensive activities such as real-time reconstruction of 3D images. These images could then be viewed locally and/or sent back to the front lines via telemetry for viewing.

EXAMPLES
(Industrial Applicability)

The invention is further illustrated by the following non-limiting examples.

Example I

A first order model (simulation) of the ultrasonic imaging system was developed to evaluate the effects of refraction and scan geometry. The model was first developed in two dimensions and later extended to three dimensions. Geometrical optics were used to determine the image geometry. The acoustic beam is modeled as a Gaussian beam and the transducer is treated as a point receiving transducer. The limb being imaged is modeled as two materials, homogeneous flesh and homogenous bone.

Despite the simplicity, the model provides useful simulated images that illustrate some of the problems that are encountered in developing an ultrasonic imaging system. The model provides a useful estimate of image distortion and image brightness. The model includes effects due to refraction, acoustic impedance, attenuation, acoustic velocity, object geometry, and scan geometry.

The following describes the elements of the computer model. The description will be developed in terms of the two dimensional model. This is adequate since reflection/refraction are inherently planar calculations, that is, the calculations are carried out in the plane of incidence. Three dimensional aspects of the problem will be addressed as appropriate.

Figure 24:
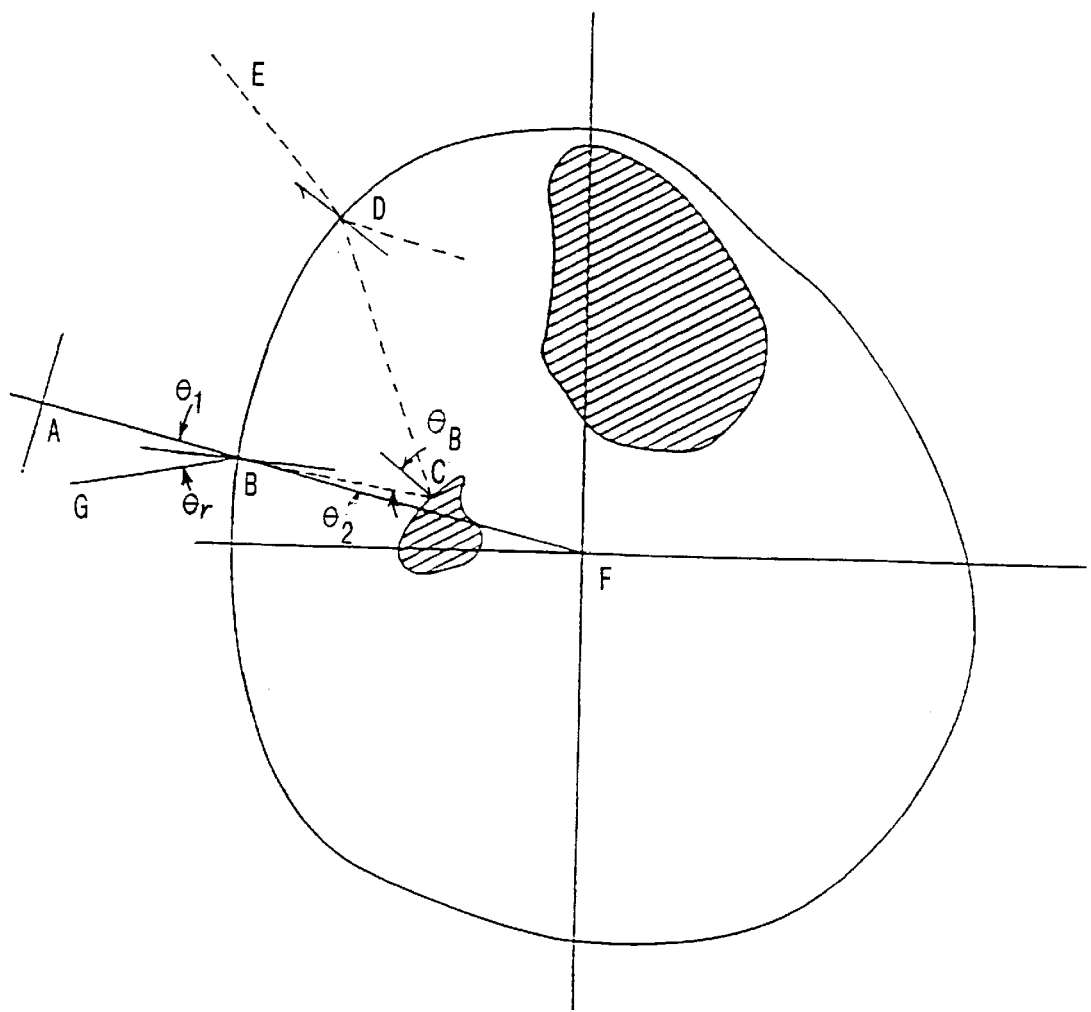
FIG. 24 shows an ultrasonic sensor geometry modeled in computer software.

The ultrasonic sensor geometry modeled in computer software of a typical leg is shown in FIG. 24.

Ultrasonic transducer 22 is located at point A with its beam direction in the direction of the line AF. There are two types of scanning that are appropriate to model; a circular scan and a more general programmable scan.

The simplest and most common type scan is a circular scan. This type of scan is determined by picking a center point F in the limb data coordinates. Transducer 22 is then located at radius AF with the beam oriented along the line AF. Transducer 22 is then rotated through 360 degrees about point F to generate the image. Scan increments are determined by the resolution and image definition requirements. The point F is a variable in the program.

The programmable scan is an option that allows the transducer position and orientation to be programmed to follow an arbitrary path. One scan geometry of interest is a linear scan where transducer 22 is moved along a line with the angle held constant. More general scans can be made up from linear scans by summing linear scans with a discrete variation in the angle variable (parameter). Another scan geometry of interest is one in which transducer 22 is scanned over a range of angles at each position along a prescribed curve.

The angles of reflection and refraction are calculated using the equations $$\theta_i = \theta_r \tag{1}$$

$$\frac{\sin\theta_i}{\sin\theta_r} = \frac{c_i}{c_r} \tag{2}$$

where the subscripts refer to the incident and reflected rays and the c's are the acoustic velocities in the corresponding medium. Distances such as AB and BC are calculated using an algorithm for computing the intersection of rays with the limb data skin and bone surfaces. The relative acoustic intensity of reflected and refracted rays are calculated using the equations $$\alpha_r = \left[ \frac{\rho_2 c_2 - \rho_1 \sqrt{c_1^2 - c_1^2 \sin^2\theta_1}}{\rho_2 c_2 + \rho_1 \sqrt{c_1^2 - c_2^2 \sin^2\theta_1}} \right]^2 \tag{3}$$

$$\alpha_t = \frac{4\rho_1 c_1 \rho_2 c_2 \cos\theta_1 \sqrt{1 - (c_2/c_1)^2 \sin^2\theta_1}}{(\rho_2 c_2 \cos\theta_1 + \rho_1 c_1 \sqrt{1 - (c_2/c_1)^2 \sin^2\theta_1})^2} \tag{4}$$

and $$\alpha_r + \alpha_t = 1 \tag{5}$$

In these equations, the numerical subscripts are ordered in the direction of the acoustic wave (ray) being considered and the $\rho$'s are the corresponding material densities.

The relative intensity of the acoustic beam is represented in angle as a Gaussian beam given by $$\beta(\phi) = \frac{I(\phi)}{I(\phi)} = \exp[-(\sin\phi/\sin\phi_0)^2] \tag{6}$$

where $$-\frac{\pi}{2} < \phi < \frac{\pi}{2} \tag{7}$$

$$\sin\phi_0 = \frac{2}{\pi} \cdot \frac{\lambda}{d_0}$$

In equation, 7, $\lambda$ is the acoustic wavelength and $d_0$ is the beam width at the beam waist (smallest width of beam). The beam width is usually taken to be the effective width of the transducer. However, the beam divergence angle can be empirically adjusted to account for scattering or receiver aperture width.

Generally, acoustic beams decrease in intensity as they propagate due to absorption and scattering. In the model beam attenuation is incorporated as an exponential decrease by the equation $$I(x) = I(O)\exp[-\eta x] \tag{8}$$

where n is the effective absorption coefficient. In its present form, the model does not include a decrease in intensity due to the divergence of the beam.

The relative image brightness determined by tracking the acoustic rays as they bounce off the various surfaces taking into account the loss of intensity due to reflection/transmission and attenuation as appropriate. The computation is illustrated for a few points in FIG. 24 by the following.

The relative image brightness of point B (relative to the transmitted intensity) in FIG. 24 is given by $$\frac{I_r(B)}{I_t} = \alpha_r \beta(2\theta_i) \qquad (9)$$

The factor of 2 in the argument of $\beta$ is due to the fact that the angle between the reflected ray and the ray returned to the transducer is twice the incident angle.

The relative brightness of the return from point C is given by $$\frac{I_r(C)}{I_t} = \alpha_t \alpha_r \beta(2\theta_B) \qquad (10)$$

where the prime denotes the transmission in the opposite direction. One then continues in this manner, keeping track of the rays as they intersect the various surfaces. Attenuation is accounted for using equation 8 and the computed distance between consecutive reflection points.

The image of point B is located a distance $$AB' = \frac{V_R}{V_{AB}} \cdot AB \qquad (11)$$

from point A along line AF. $V_R$ is the reference acoustic wave velocity. Similarly, the image point location of point C is given by the distance.

$$AC' = \frac{V_R}{V_{AB}} \cdot AB + \frac{V_R}{V_{AB}} \cdot BC \qquad (12)$$

again, along line AF.

The two dimensional ultrasound simulation package is a C/C++ program that applies ultrasonic computation and image generation mathematics to mock ultrasound beams and predetermined tank and body part such as leg geometries. The calculations are applicable to a plane containing both the incident and scattered beam and a two dimensional leg model. A model is created of the acoustic properties of both the ultrasound beam and the materials it travels through with sufficient fidelity to predict the salient characteristics of the ultrasound image. The basic equations used in the simulation are given above.

The algorithm requires input from leg and scan tub geometries along with the ultrasound beam parameters such as where the scans originate from, the direction they travel, and the strength of the beam.

It also requires the acoustic properties of the materials in each region (i.e., water, muscle, bone, etc.).

This is a collection of C and C++ programs with a Devguide based user interface. The output displays are done using Gnuplot windows. Beams are traced using recursive calls on reflected and transmitted components of rays as they intersect surfaces in the simulation. The return is always assumed along the incident beam path.

A typical menu for the two dimensional simulator with details for each of the field/buttons are as follows:

Coordinates of the center of the leg: This field allows the user to specify the X,Y coordinates of the center of the object being scanned. The coordinate parameters allow the object to be placed at various locations in the tank during the simulated scan.

Nominal speed of sound (cm/sec): This field allows the user to declare the nominal speed of sound in water.

Frequency in Hz: This field allows the user to specify the frequency of the simulated ultrasound beam.

Lower limit of return signal: This field sets the lower limit of signal strength for return beams to be detectable. Initial transmitted power: This field sets the power of the initial beam transmission.

Focus beam radius (cm): This field sets the radius of the beam width at the beam waist.

Max time for return signals: This field sets the maximum duration of time allowable for return signals to be detected.

Number of sensors in scan: This field sets the number of discrete locations (or stops) from which scans are done. They are concentrically located around the "tub".

Create scan path: This field initiates the creation and execution of the simulation using the specified parameters, generating a file containing the output results.

Display plot: This field causes one of two types of display to appear. If simulated data, or CT data, have been chosen on "Data type," a Gnuplot window displays the results of the simulation run. If "three dimensional view" is selected, it causes a three dimensional grid display of the stored CT geometry but without scan data. Data type:

Simulated data—selects simulated data for the scan—either a leg model or circles.

CT data—selects leg geometries obtained from actual CT scans for the simulation. The user may choose any of the available CT cuts.

Three Dimensional View—allows display of a three dimensional view of the "CT data."

Model type: When "simulated data" is selected under "Data type", "Model Type" allows you to select either a leg model or circles for the scanned object.

Number of sweep scans: This field selects the number of actual angular scans taken at each of the stops in the scan (at each of the discrete locations of the scanner).

Sweep angle: The angle over which the "number of sweep scans" is uniformly distributed at each of the discrete scan locations.

Figure 25:
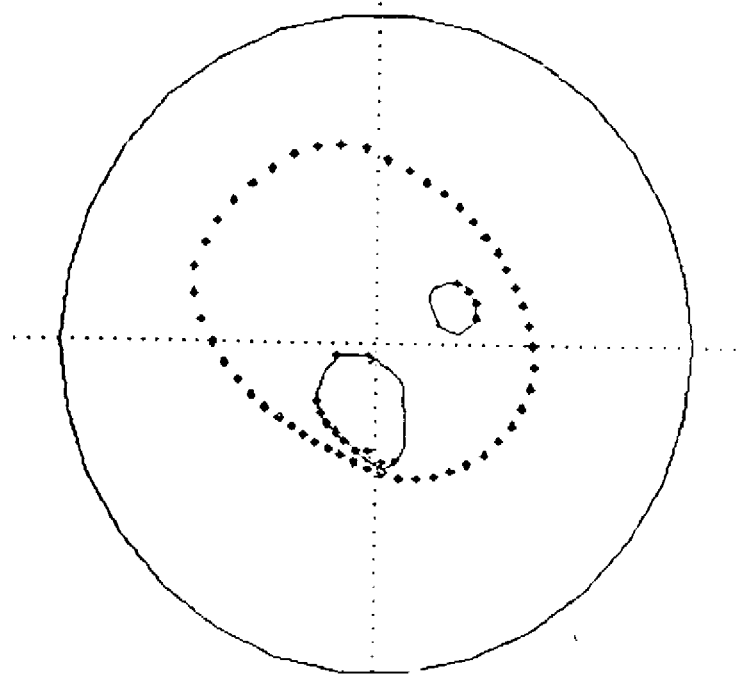
FIG. 25 is a simulated leg geometry with 50 sensors and 1 scan per sensor.
Figure 26:
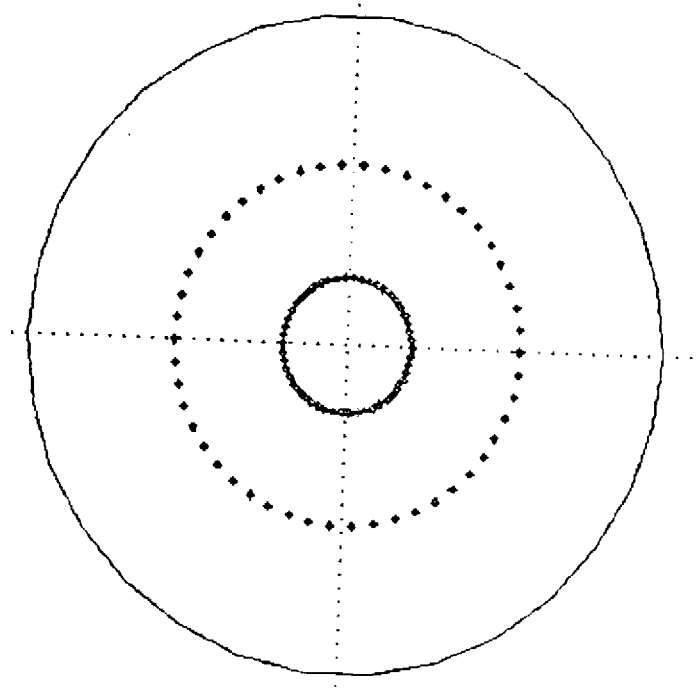
FIG. 26 is a simulated circle geometry with 50 sensors and 1 scan per sensor.
Figure 27:
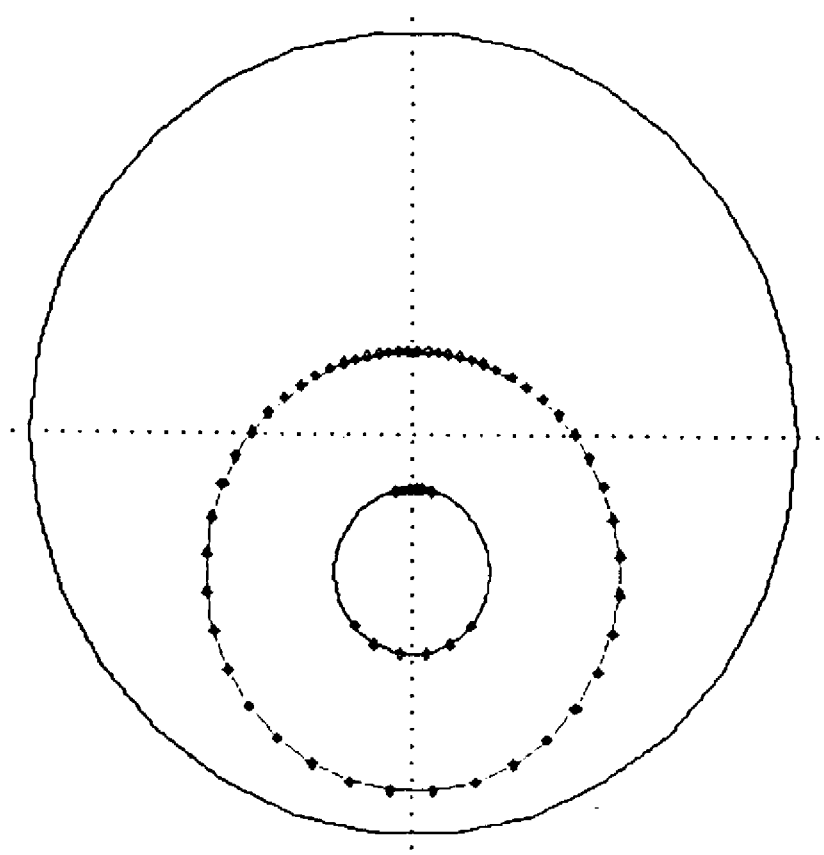
FIG. 27 is a simulated offset center circle geometry with 50 sensors and 1 scan per sensor.
Figure 28:
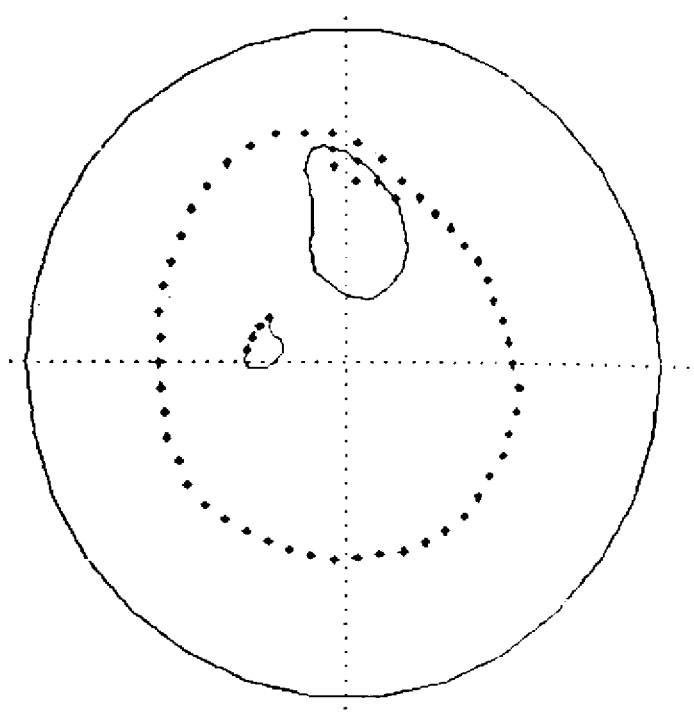
FIG. 28 is an actual CT data scan.
Figure 29:
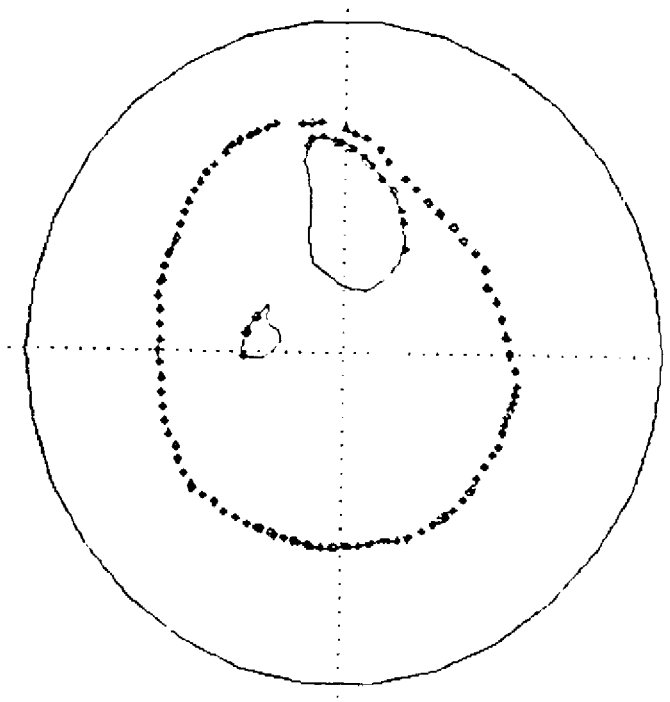
FIG. 29 is demonstrates the use of multiple scans (5) at each of 30 sensors.

FIGS. 25–29 are examples of the simulation. FIG. 25 is an example of simulated leg geometry with 50 sensors, 1 scan per sensor using simulated leg geometries. FIG. 26 shows 50 sensors, 1 scan per sensor for a circle. FIG. 27 is a simulated offset center circle. FIG. 28 is an actual CT scan. FIG. 29 shows 5 scans at each of 30 sensors.

The three dimensional model uses logic similar to the two dimensional model, but it extends into three dimensions. The differences include scan beams that have X,Y,Z components to both their origin and their direction. Points of intersection occur between three dimensional vectors and planes, as opposed to lines contained in the Z=0 plane, and, therefore, may have components in the Z direction. Finding the points of intersection is much more involved, and, consequently, the run time is much greater. Because the time constraints, this algorithm has only been implemented in batch mode with precalculated fixed scan parameters. The data input for the three dimensional mode contain:

a file containing the parameters of the scan beams which includes the origin and direction (in three dimensional space) as well as the beam strength, created by a separate algorithm; and separate files for tank and leg geometries which define the three dimensional surfaces of the objects.

The three dimensional simulation is a batch mode C program which uses three dimensional vector geometry to trace the beams with recursive calls on the reflected and transmitted components of rays that result from intersections with object surfaces. Rays are terminated when their power has dropped below a predetermined threshold, or are absorbed by the tank wall. Return signals are calculated at each intersection; again, assume a return along the incident beam path. Output is a file of three dimensional points.

Figure 30:
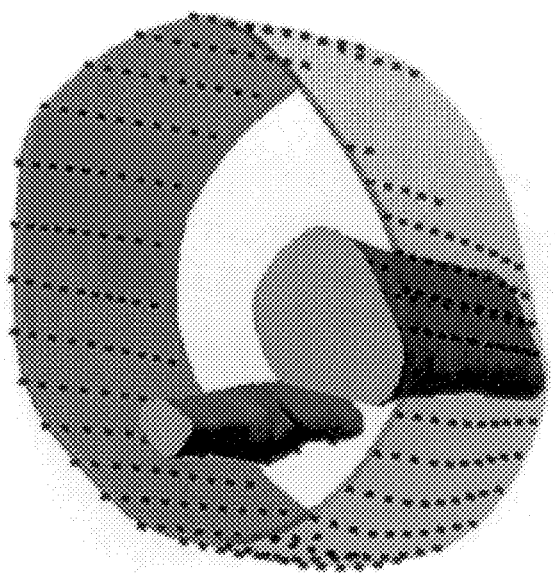
FIG. 30 is a three dimensional rendering of a leg.

FIG. 30 shows the output points displayed as small black cubes with the three dimensional rendering of the skin and bone surfaces used in the scan.

Because the ultrasound machine provides a planar image that represents a cross-sectional view of the object, an additional spatial dimension must be imparted to the transducer in order to generate a three dimensional, volumetric image. The mechanical scanner provides the additional scanning motion necessary to develop the third dimension of the image. The scanner is designed based on the results of the computer model which concluded that a circular scan around a BK limb is sufficient for providing skin and partial bone surface information.

Example II

The 3D ultrasound imaging system was tested on 10 unilateral below-the-knee amputees at the Health Science Center in San Antonio. Image data was acquired from both the sound limb and the residual limb. The imaging system was operated in both volumetric and planar formats. An x-ray CT scan was performed on each amputee for comparison. Qualitative and quantative studies were performed to compare CT and ultrasound data sets. Results of the test indicate beneficial use of ultrasound to generate databases for fabrication of prostheses at a lower cost and with better initial fit as compared to manually fabricated prostheses. In addition, qualitative results indicate that planar images represent substantial improvements over standard ultrasound images and that they could serve as improved diagnostic images.

In general, the human subjects placed their legs within the water bath while holding onto the support railing. The ultrasound gains were set for optimum image quality. Images were stored on the computer for later retrieval and manipulation.

These ten subjects made up of 5 women and 5 men provided databases for establishing the repeatability and quality of the ultrasound scanning system. Each subject was scanned using the vertical and horizontal oriented transducer. Each leg on the subject was scanned to double the effective data set. The system was fine-tuned based on the results of the scans.

After each data set was obtained, the images were processed through the visualization software used to generate a composite image. For the men in the study, leg hair posed a problem for image acquisition. Leg hair tends to trap air bubbles and turned to blur the definition of the skin surface. The volunteers opted to wear women's leg hosiery to keep the leg hair close to the skin rather than shaving the leg. Movement, high reflection at the surface of the sock, and poor centering were corrected for. Modifications in the scan procedure were made based on the "lessons learned" during the scans as well as improvements to the visualization software. The result of this exercise was an improved image acquisition procedure and improved visualization software.

Figure 31:
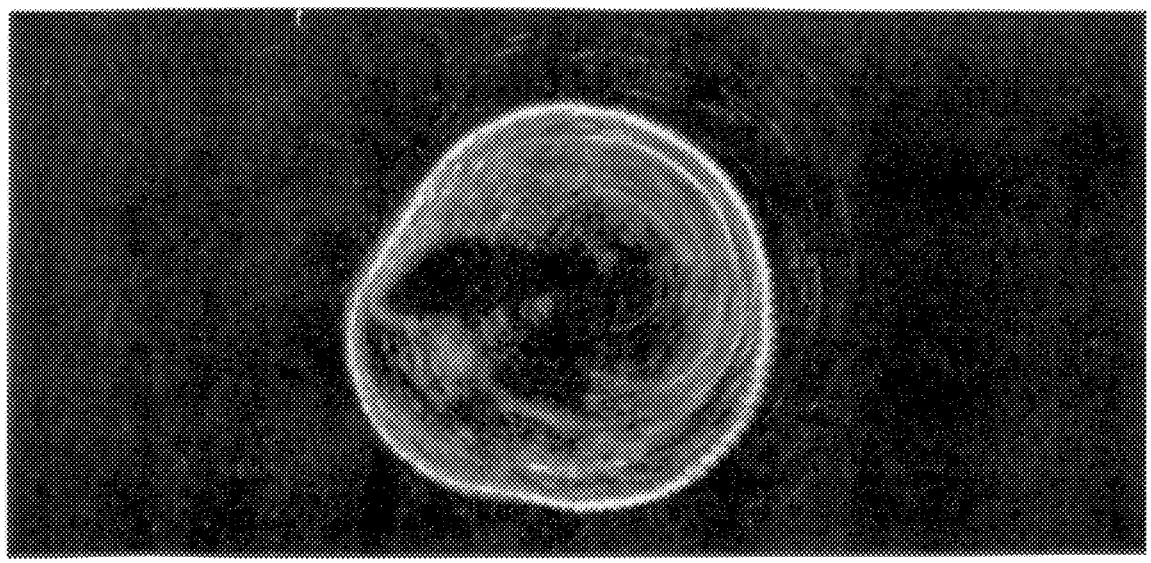
FIG. 31 is an ultrasound cross-section.
Figure 32:
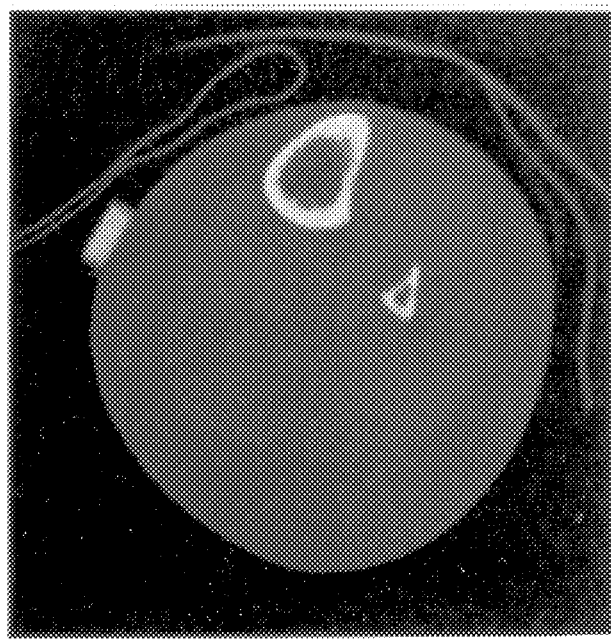
FIG. 32 is a CT cross-section.

Algorithms were developed to "edge" accurately the two dimensional ultrasound cross-section images reconstructed from the vertical scans and the two dimensional CT cross sections. See FIGS. 31 and 32 for examples of the ultrasound and CT images.

Figure 33:
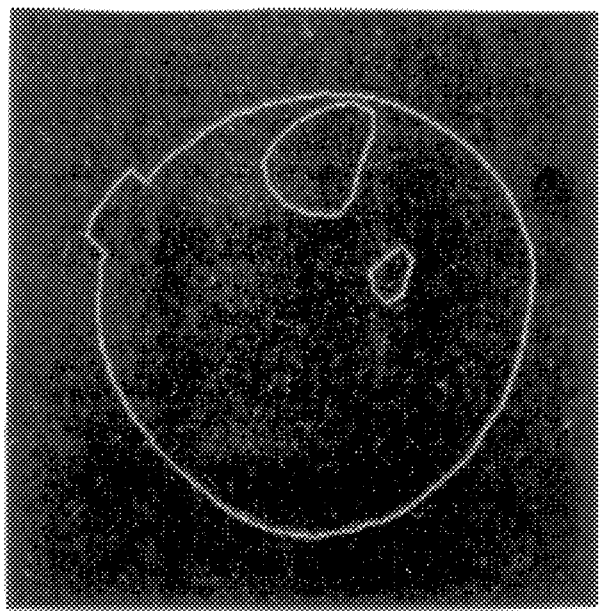
FIG. 33 is a resulting edge from a CT scan.

The outlines obtained from the ultrasound process can then be used to produce three dimensional models of the leg. The images are first brought to a threshold to eliminate noise in and around the leg cross section. The edging algorithm starts from a "first" valid point, usually chosen by the user. From that point, the algorithm searches for the next point on the edge within a bounding box of specified size. The initial perpendicular to the surface at that point is assigned at 180. Vectors are defined from the first point to each point in the bounding box. The next valid point on the edge is chosen as the one with the smallest vector angle with respect to the perpendicular. Continuing around the leg, angles are computed to the points contained in the bounding box with respect to a perpendicular to the edge created by the last two valid points. The next point chosen on the edge is the one with the smallest angle. The process continues around the leg until the first point on the edge is contained within the bounding box, indicating the completion of the edge. See FIG. 33 for an example of a resulting edge from a CT scan.

This edging algorithm is used for edging the CT scans, including skin, tibia, and fibula, all of which must be done separately. The algorithm is also used for edging the ultrasound skin image, but cannot be used for the bones in the ultrasound images. The ultrasound images are somewhat coarse, and the bones are "incomplete" on the inside of the leg where the ultrasound has been reflected and attenuated by the bone, shading the back portion of the bone. Therefore the only valid bone data on the ultrasound scans is that near the surface or skin of the leg. Instead of using the automated edging algorithm, the bone images must be edged by "placing and re-sizing" templates of the bones on each cross-section. The marker affixed to the skin is visible at the upper right edge of the image in FIG. 31.

A graphical user interface (GUI) was designed which allows the user to compare qualitatively images obtained with the ultrasound platform to the CT images obtained. The interface was written for use on a Silicon Graphics (SGI) machine, using "Forms" (SGI software for creating windows, buttons and other user interfaces), Graphics Language, and C programming.

With the GUI, the user can load a series of images for a particular patient: ultrasound, CT, and edge points created by the edging routine. See FIG. 31 for an example of an image viewed using the GUI. The user may "browse" through the series of ultrasound or CT cross-sections image by image. In order to make a comparison, the user may, for instance, display an ultrasound image at a particular position on the leg. Next, the user can display the CT edge image, generated from the corresponding CT scan taken at approximately the same position on the patient's leg, overlaid in red on top of the ultrasound image. Features such as "click and drag", rotation, mirror, and scale are incorporated in the edge image display in order to properly line it up with the corresponding ultrasound image. Once it has been positioned for the "best fit", a visual comparison can be made of the proportions and positions of the features in the leg.

Because of problems present with leg deformation in the CT scans (due to parts of the leg being supported during scanning), making comparisons between the ultrasound and CT scans is difficult. Two dimensional comparisons are greatly affected by any deformation since displaced tissue can cause cross-sections taken at the same position on the leg to look very different. It was decided that three dimensional volumetric comparison methods would give more accurate results than two dimensional scan-by-scan comparisons. The theory behind this idea was that if any deformation occurred at a point on the leg, the tissue would be displaced a small distance away from its usual position. By examining the entire volume of the leg model, any individual tissue displacements should not affect the overall volume calculation.

Figure 34:
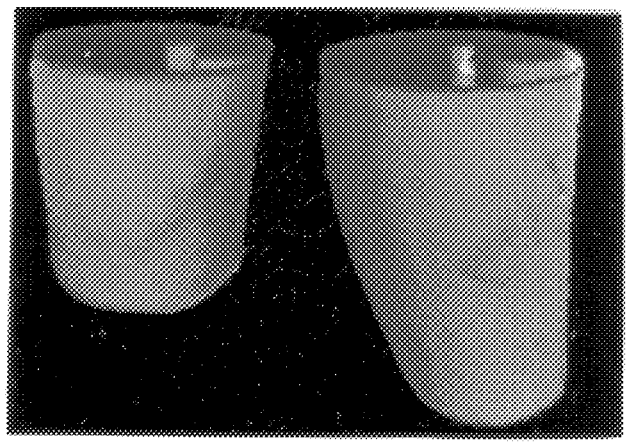
FIG. 34 is a side view of comparisons of three dimensional ultrasound and CT solid models.
Figure 35:
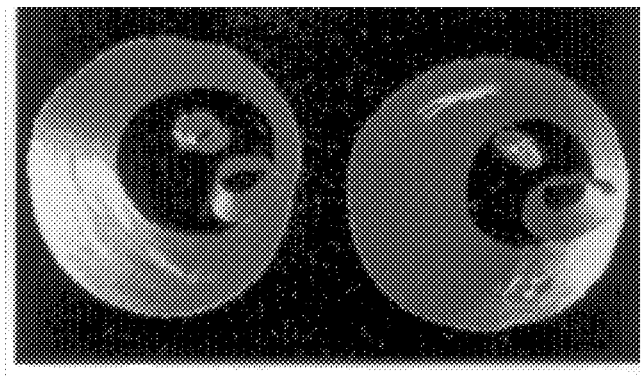
FIG. 35 is a top view of the models of FIG. 34.
Figure 36:
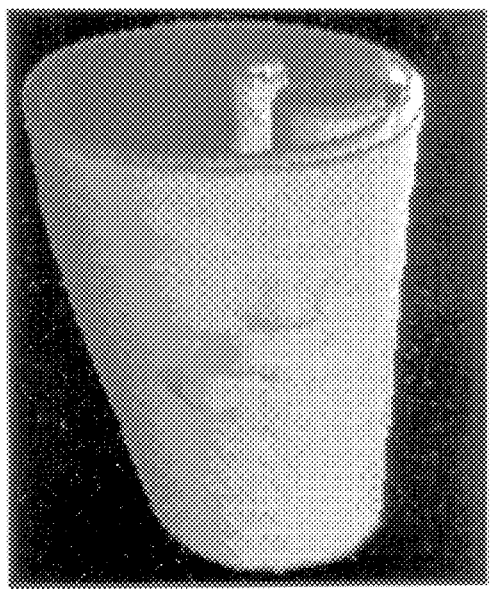
FIG. 36 is a side view of a registered ultrasound and CT volume.
Figure 37:
FIG. 37 is a top view of the volume of FIG. 36.

Another GUI was created which displays three dimensional wire frame and solid polygon models generated from both ultrasound and CT images. See FIGS. 34 and 35 for an example of a comparison of ultrasound and CT three dimensional solid models. Edge points from the ultrasound and CT images for the specified patient are loaded by the application. The user can rotate and translate the models in order to facilitate viewing or to align the models for comparisons. The application contains a routine developed to iteratively orient the corresponding CT and ultrasound volumetric models by rotating and translating for the best geometric fit. Three dimensional point sets from the ultrasound data are registered with corresponding three dimensional point sets from CT scans. The two models can be registered by their entire volumes or only their intersecting length portion. If the ultrasound and CT models are separated initially, they should be registered based on their entire volumes since there is no intersection. If, however, the models have been approximately registered by the user beforehand, using the registration based on their intersection will refine the pose of the ultrasound point sets to find the best registration. See FIGS. 36 and 37 for examples of the ultrasound and CT models after registration.

The point sets are registered based on Besl and McKay's (Besl & McKay, 1992) "iterative closest point" (ICP) algorithm. This algorithm searches for the minimum mean-squared distance between the two point sets. For each point in the moveable point set (ultrasound in this case), it finds the closest point in the stationary point set (in this case CT). The ICP then computes a transformation matrix to minimize the distances between the matched points. The moveable points are moved according to this computed transform. This process of matching and moving is repeated until the mean-squared distance cannot be reduced any further.

Once the models are properly registered, a quantitative volumetric comparison can be made. In order to accurately compare the volumes of the ultrasound and CT three dimensional models, only the intersecting length portions of the two volumes are considered. This process is necessary because the CT volumes often represent a much longer portion of the leg than the ultrasound data. The volumes of the two models are then calculated, and a percent difference value is given.

The preceding examples can be repeated with similar success by substituting the generically or specifically described reactants and/or operating conditions of this invention for those used in the preceding examples.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above, and of the corresponding applications, are hereby incorporated by reference.

What is claimed is:

1. An apparatus for generating a video presentation of ultrasound images of an object, the apparatus comprising:
    a multielement ultrasound transducer that radiates ultrasound energy in a first plane;
    means to move the transducer about the object in a second plane;
    means for acquiring at least one plurality of partially redundant ultrasound images in the first plane in scan increments of the object;
    means for converting said acquired images into a selected format;
    means for storing said converted images; and
    means for registering said converted images to generate a composite image of the object.

2. The invention of claim 1 wherein said at least one ultrasound transducer comprises a two dimensional array of ultrasound transducers.

3. The invention of claim 1 wherein said means for acquiring at least one plurality of partially redundant ultrasound images in the first plane comprises a means for acquiring data from known orientations and positions.

4. The invention of claim 3 wherein said orientations comprise angles from a home orientation.

5. The invention of claim 3 wherein said means for acquiring data from known orientations and positions comprises feedback means for optimizing a next scan.

6. The invention of claim 5 wherein said feedback means comprises a means for reorienting said at least one ultrasound transducer based on a previous scan's signal quality.

7. The invention of claim 3 wherein said means for acquiring data from known orientations and positions comprises a filter means for acquired data reduction.

8. The invention of claim 7 wherein said filter means comprises rank value filtering.

9. The invention of claim 3 wherein said means for acquiring data from known orientations and positions comprises a position transducer.

10. The invention of claim 9 wherein said position transducer comprises a member selected from the group of encoders, potentiometers, LVDT'S, resolvers, magnetic encoders, and inductosync apparatuses.

11. The invention of claim 10 further comprising a tachometer.

12. The invention of claim 11 wherein said means for registering further comprises a means for object motion compensation.

13. The invention of claim 3 wherein said means for acquiring data from known orientations and positions comprises means for determining coordinates for selected targets within the object from said converted images.

14. The invention of claim 1 wherein said partially redundant ultrasound images comprise vertical partially redundant images.

15. The invention of claim 1 wherein said partially redundant images comprise horizontal partially redundant images.

16. The invention of claim 1 wherein said partially redundant images comprise partially redundant images in any known angle between horizontal and vertical.

17. The invention of claim 1 wherein said scan increments comprise surface normal optimization.

18. The invention of claim 17 wherein said means for object motion compensation comprises correlating partially redundant image data.

19. The invention of claim 1 wherein said scan increments comprise said composite image with an optimized intensity of predetermined anatomical features of the object.

20. The invention of claim 1 wherein said means for registering comprises a transformation matrix means for realignment of converted image data relative to home position orientation.

21. A method of generating a video presentation of ultrasound images of an object, the method comprising the steps of:
    a) providing a multielement ultrasound transducer radiating in a first plane;
    b) moving the transducer about the object in a second plane;
    c) acquiring at least one plurality of partially redundant ultrasound images in a same plane in scan increments of the object;

d) converting said acquired images into a selected format;

e) storing said converted images; and f) registering said converted images to generate a composite image of the object.

22. The method of claim 21 wherein the step of providing at least one ultrasound transducer comprises providing a two dimensional array of ultrasound transducers.

23. The method of claim 21 wherein the step of acquiring at least one plurality of ultrasound images comprises acquiring data from known orientations and positions.

24. The method of claim 23 wherein the step of acquiring data from known orientations comprises acquiring angle data from a home orientation.

25. The method of claim 23 wherein the step of acquiring data from known orientations and positions comprises optimizing a next scan with feedback from a prior scan.

26. The method of claim 25 wherein the feedback comprises reorienting the at least one transducer based on a previous scan's signal quality.

27. The method of claim 23 wherein the step of acquiring data from known orientations and positions comprises providing a filter for acquired data reduction.

28. The method of claim 27 wherein the filter comprises rank value filtering.

29. The method of claim 23 wherein the step of acquiring data from known orientations and positions comprises providing a position transducer.

30. The method of claim 29 wherein the step of providing a position transducer comprises providing a member selected from the group of encoders, potentiometers, LVDT's, resolvers, magnetic encoders, and inductosync apparatuses.

31. The method of claim 29 further comprising the step of providing a tachometer.

32. The method of claim 23 wherein the step of acquiring data from known orientations and positions comprises determining coordinates for selected targets within the object from the converted images.

33. The method of claim 21 wherein the step of acquiring at least one plurality of partially redundant images comprises acquiring at least one plurality of partially redundant vertical images.

34. The method of claim 21 wherein the step of acquiring at least one plurality of partially redundant images comprises acquiring at least one plurality of partially redundant horizontal images.

35. The method of claim 21 wherein the step of acquiring at least one plurality of partially redundant images comprises acquiring at least one plurality of partially redundant images in any known angle between horizontal and vertical.

36. The method of claim 21 wherein the step of acquiring at least one plurality of partially redundant ultrasound images in the first plane in scan increments comprise optimizing surface normal.

37. The method of claim 21 wherein the step of acquiring at least one plurality of partially redundant ultrasound images in the first plane in scan increments comprises optimizing the intensity of predetermined anatomical features of the object from the composite image.

38. The method of claim 21 wherein the step of registering comprises realigning the converted image data relative to home position orientation with a transformation matrix.

39. The method of claim 38 wherein the step of registering further comprises compensating for object motion.

40. The method of claim 39 wherein the step of compensating for object motion comprises correlating partially redundant image data.

* * * * *